(12) United States Patent
Kumar et al.

(10) Patent No.: US 8,637,670 B2
(45) Date of Patent: Jan. 28, 2014

(54) IMIDAZO [4,5-C]QUINOLINE DERIVATIVES AND THEIR USE IN THE TREATMENT OF TUMORS AND/OR INFLAMMATION

(75) Inventors: Sanjay Kumar, Maharashtra (IN); Ram Vishwakarma, Jammu (IN); Ramswaroop Mundada, Maharashtra (IN); Vijaykumar Deore, Maharashtra (IN); Pramod Kumar, Maharashtra (IN); Somesh Sharma, Maharashtra (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/381,464

(22) PCT Filed: Jun. 30, 2009

(86) PCT No.: PCT/IB2009/052819
§ 371 (c)(1),
(2), (4) Date: Dec. 29, 2011

(87) PCT Pub. No.: WO2011/001212
PCT Pub. Date: Jan. 6, 2011

(65) Prior Publication Data
US 2012/0108627 A1    May 3, 2012

(51) Int. Cl.
*C07D 471/12*    (2006.01)
*A61K 31/122*    (2006.01)

(52) U.S. Cl.
USPC .......................................... 546/82; 514/676

(58) Field of Classification Search
USPC .............................. 544/106; 546/82; 514/676
See application file for complete search history.

(56) References Cited

FOREIGN PATENT DOCUMENTS

| WO | WO-03/097641 | * 11/2003 |
| WO | 2006/122806 A2 | 11/2006 |
| WO | WO-2006122806 | * 11/2006 |

* cited by examiner

*Primary Examiner* — Yong Chu
*Assistant Examiner* — Sonya Wright
(74) *Attorney, Agent, or Firm* — Ladas & Parry LLP

(57) ABSTRACT

The present invention provides the compounds of formula (I):

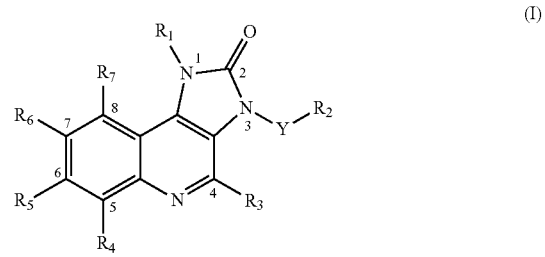

The present invention relates to imidazo[4,5-c]quinoline derivatives of formula (I), process for their preparation, pharmaceutical compositions containing them and their use in the treatment of diseases mediated by phosphatidylinositol-3-kinase (PBK) and/or mammalian target of rapamycin (mTOR) and/or tumor necrosis factor-α (TNF-α) and/or interleukin-6 (IL-6), particularly in the treatment of cancer and inflammation.

13 Claims, No Drawings

US 8,637,670 B2

IMIDAZO [4,5-C]QUINOLINE DERIVATIVES AND THEIR USE IN THE TREATMENT OF TUMORS AND/OR INFLAMMATION

This is a 371 application of PCT/IN2009/052819 filed on Jun. 30, 2009, the content of which is incorporated herein by reference.

FIELD OF THE INVENTION

The present invention relates to imidazo[4,5-c]quinoline derivatives, processes for their preparation, pharmaceutical compositions containing them and their use in the treatment of diseases mediated by phosphatidylinositol-3-kinase (PI3K) and/or mammalian target of rapamycin (mTOR) and/or tumor necrosis factor-α (TNF-α) and/or interleukin-6 (IL-6), particularly in the treatment of cancer and inflammation.

BACKGROUND OF THE INVENTION

Cancer is an uncontrolled growth and spread of cells that may affect almost any tissue of the body. More than eleven million people are diagnosed with cancer every year. It is estimated that there will be sixteen million new cases every year by 2020. Cancer causes seven million deaths every year worldwide.

Cancer can be defined as abnormal growth of tissues characterized by a loss of cellular differentiation. It is caused due to a deregulation of the signaling pathways involved in cell survival, cell proliferation and cell death.

Current treatments for cancer have limited effectiveness and a number of side effects. Cancer therapy currently falls under the following categories including surgery, radiation therapy, chemotherapy, bone marrow transplantation, stem cell transplantation, hormonal therapy, immunotherapy, anti-angiogenic therapy, targeted therapy, gene therapy and others.

Activation of phosphatidylinositol-3-kinase (PI3K) results in a disturbance of control of cell growth and survival, and hence this pathway is an attractive target for the development of novel anticancer agents (Nat. Rev. Drug Discov., 2005, 4, 988-1004). The mammalian target of rapamycin (mTOR) regulates cell growth and metabolism in response to environmental cues hence inhibitors of mTOR may be useful in the treatment of cancer and metabolic disorders (Cell, 2006, 124, 471-484).

PI3K mediated signaling pathway plays a very important role in cancer cell survival, cell proliferation, angiogenesis and metastasis. The PI3K pathway is activated by stimuli such as growth factors, hormones, cytokines, chemokines and hypoxic stress. Activation of PI3K results in the recruitment and activation of protein kinase B (AKT) onto the membrane, which gets phosphorylated at Serine 473 (Ser-473). Thus, phosphorylation of Ser-473 of AKT is a read-out/detector for the activation of the PI3K-mediated pathway. A cell-based ELISA technique can be used to study such activation.

AKT is known to positively regulate cell growth (accumulation of cell mass) by activating the mTOR serine threonine kinase. mTOR serves as a molecular sensor that regulates protein synthesis on the basis of nutrients. mTOR regulates biogenesis by phosphorylating and activating p70S6 kinase (S6K1), which in turn enhances translation of mRNAs that have polypyrimidine tracts. The phosphorylation status of S6K1 is a bonafide read-out of mTOR function.

Most tumors have an aberrant PI3K pathway (Nat. Rev. Drug Discov., 2005, 4, 988-1004). Since mTOR lies immediately downstream of PI3K, these tumors also have hyperactive mTOR function. Thus, most of the cancer types will potentially benefit from molecules that target PI3K and mTOR pathways.

The compounds that are PI3K and/or mTOR inhibitors, find use in the treatment of cancers. Compounds are used to reduce, inhibit, or diminish the proliferation of tumor cells, and thereby assist in reducing the size of a tumor. Representative cancers that may be treated by such compounds include but are not limited to bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, acute lymphoblastic leukemia, acute myeloid leukemia, liver cancer, medulloblastoma, neuroblastoma, brain tumors, non-Hodgkin's lymphoma, mantle cell lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

SF 1126 (Semaphore, Inc.) is in phase I clinical trials. SF1126 is a covalent conjugate of LY294002 containing a peptide-based targeting group. In vivo, it gets converted spontaneously at physiologic pH to LY294002 which is a viable version, and as a prodrug, it is able to block PI3K without affecting the normal cells. GDC-0941 (Piramed Ltd. and Genentech, Inc.) is a PI3K inhibitor and is in phase I clinical trials. BEZ-235 (Novartis AG), which is currently in phase I/II clinical trials, inhibits all isoforms of PI3K and also inhibits the kinase activity of mTOR. XL-765 (Exelixis, Inc.) is also a dual inhibitor of mTOR and PI3K. The compound is in phase I clinical trials as an oral treatment for solid tumors.

Inflammation is the response of a tissue to injury that may be caused by a biological assault such as invading organisms and parasites, ischemia, antigen-antibody reactions or other forms of physical or chemical injury. It is characterized by increased blood flow to the tissue, causing pyrexia, erythema, induration and pain.

Several proinflammatory cytokines, especially TNF-α and interleukins (IL-1 β, IL-6, IL-8) play an important role in the inflammatory process. Both IL-1 and TNF-α are derived from mononuclear cells and macrophages and in turn induce the expression of a variety of genes that contribute to the inflammatory process. An increase in TNF-α synthesis/release is a common phenomenon during the inflammatory process. Inflammation is an inherent part of various disease states like rheumatoid arthritis, Crohn's disease, ulcerative colitis, septic shock syndrome, atherosclerosis, among other clinical conditions.

TNF-α has been implicated as a mediator in inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma. Much research has been conducted to study the effect of TNF-α and anti-TNF-α therapies. Studies in the area of cancer have shown that with TNF-α therapy it is important to balance the cytotoxicity and systemic toxicity of the potential drug candidates.

Rheumatoid arthritis (RA)—an autoimmune disorder, is a chronic, systemic, articular inflammatory disease in which the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, feet and ankles. Cartilage destruction in RA is linked to aberrant cytokines (e.g. TNF-α and IL-6) and growth factor expression in the affected joints.

The first line of treatment for inflammatory disorders involves the use of non-steroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of disorder and not the cause. When patients fail to respond to NSAIDs, other drugs such as methotrexate, gold salts, D-penicillamine and corticosteroids are used. These drugs also have significant toxic effects. Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

WO2005/054237 describes 1H-imidazoquinoline derivatives for use in the treatment of protein kinase dependent diseases such as benign or malignant tumor.

WO2006/122806 describes imidazoquinolines as lipid kinase inhibitors that are used alone or in combination with one or more other pharmaceutically active compounds for the treatment of an inflammatory or obstructive airway disease such as asthma or a proliferative disease such as a tumor disease.

WO 2003/097641 describes the use of imidazoquinolines in the treatment of protein kinase dependent diseases.

SUMMARY OF THE INVENTION

According to one aspect of the present invention there are provided compounds of formula (I) (as described herein below).

According to another aspect there are provided compounds of formula (I), which are inhibitors of PI3K and/or mTOR mediated signaling.

According to a further aspect, there are provided compounds formula (I) which are inhibitors of proinflammatory cytokines such as TNF-α and/or IL-6.

According to another aspect there are provided processes for producing compounds of formula (I).

According to a further aspect there is provided use of compounds of formula (I) or compositions containing compounds of formula (I) or compositions manufactured using compounds of formula (I) for the treatment of cancers such as breast cancer, leukemia, lung cancer and gastric cancer, prostate cancer, pancreatic cancer, glioblastoma, colon cancer, head and neck squamous cell carcinoma, multiple myeloma, cervical carcinoma and melanoma.

According to further aspect there is provided use of compounds of formula (I) or compositions containing compounds of formula (I) or compositions manufactured using compounds of formula (I) for the treatment of inflammation, including diseases such as rheumatoid arthritis, Crohn's disease, ulcerative colitis, septic shock syndrome, psoriasis and atherosclerosis.

According to another aspect of the present invention there is provided a method for treatment of cancer comprising administering to a mammal in need thereof a therapeutically effective amount of compounds of formula (I).

According to another aspect of the present invention there is provided a method for treatment of inflammation comprising administering to a mammal in need thereof a therapeutically effective amount of compounds of formula (I).

These and other objectives and advantages of the present invention will be apparent to those skilled in the art from the following description.

DETAILED DESCRIPTION OF THE INVENTION

The present invention provides the compounds of formula (I):

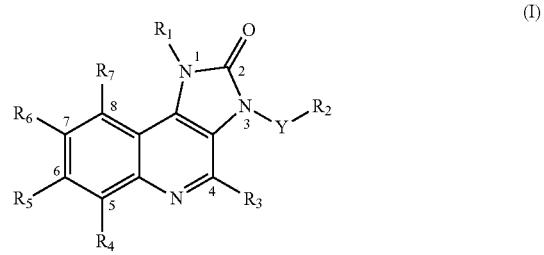

in all their stereoisomeric and tautomeric forms and mixtures thereof in all ratios, their pharmaceutically acceptable salts and pharmaceutically acceptable solvates,
wherein,
$R_1$ is aryl, which is unsubstituted or substituted with an alkyl group, wherein the alkyl group is unsubstituted or substituted with one or more of the same or different groups selected from nitro, cyano, —CONH$_2$, amino, halogen, hydroxy, haloalkyl and alkoxy;
$R_2$ is alkyl, alkenyl, alkynyl, cycloalkyl, aryl, heterocyclyl, heteroaryl, amino, —NHR$_8$ or —NR$_8$R$_8$;
$R_3$, $R_4$, $R_5$ and $R_7$ are each independently selected from hydrogen, alkyl, alkenyl, alkynyl, cycloalkyl, aralkyl, halogen, acyl, hydroxy, alkoxy, amino, cyano and nitro;
$R_6$ is hydrogen, alkyl, alkenyl, alkynyl, cycloalkyl, aralkyl, halogen, acyl, hydroxy, amino, cyano, nitro, thiol, —COOH, —CONH$_2$, —OR$_8$, —NHR$_8$, —SR$_8$ or —B(OH)$_2$;
each $R_8$ is independently selected from alkyl, alkenyl, alkynyl, cycloalkyl, aralkyl, aryl, heteroaryl or heterocyclyl; and
Y is —C(O), —C(S) or —S(O)$_n$, wherein n is 0, 1 or 2;

wherein alkyl is unsubstituted or substituted by one or more of the same or different groups such as halogen, nitro, cyano, imino, amino, hydroxy, carbonyl, carboxy, ester, ether, alkyl, alkoxy, cycloalkyl, alkylthio, thioester, sulfonyl, aralkyl, acyl, acyloxy, —$CONH_2$, heterocyclyl, aryl and heteroaryl;

alkenyl is unsubstituted or substituted by one or more of the same or different groups such as halogen, hydroxy, carboxy, acetoxy, amino, cyano, nitro, acyl, alkyl, haloalkyl, cycloalkyl, alkoxy, aryloxy, aryl, aralkyl and heterocyclyl;

alkynyl is unsubstituted or substituted by one or more of the same or different groups such as alkyl, halogen, hydroxy, carboxy, acetoxy, amino, cyano, nitro, acyl, haloalkyl, cycloalkyl, alkoxy, aryloxy, aryl, aralkyl and heterocyclyl;

cycloalkyl is unsubstituted or substituted by one or more of the same or different groups such as halogen, nitro, cyano, imino, amino, hydroxy, carbonyl, carboxy, ester, ether, alkyl, alkoxy, cycloalkyl, alkylthio, thioester, sulfonyl, haloalkyl, aralkyl, acyl, acyloxy, —$CONH_2$, lower alkyl, heterocyclyl, aryl and heteroaryl;

aryl is unsubstituted or substituted by one or more of the same or different groups such as halogen, hydroxy, alkyl, amino, cyano, nitro, thiol, —$CONH_2$, carbonyl, sulfonyl, haloalkyl, acyl, alkoxy, haloalkoxy, trifluoromethoxy, aryloxy and aryl;

heteroaryl is unsubstituted or substituted by one or two of the same or different groups such as cyano, nitro, halogen, alkyl, haloalkyl, hydroxy, alkoxy, amino, —$CONH_2$, cycloalkyl, carboxy, acyl and aryl;

heterocyclyl is unsubstituted or substituted by one or more of the same or different groups such as alkyl, alkoxy, trifluoromethoxy, halogen, hydroxy, hydroxyalkyl, haloalkyl, aryloxy, amino, cyano, nitro, thiol, carbonyl, sulfonyl, carboxy, acyl, heterocyclyl, aryl, —$CONH_2$ and —$NHR_8$.

The present invention also relates to a process for the preparation of the compounds of formula (I), their pharmaceutically acceptable salts, their pharmaceutically acceptable solvates, pharmaceutically acceptable polymorphs and pharmaceutical compositions containing them.

Definitions

Listed below are definitions, which apply to the terms as they are used throughout the specification and the appended claims (unless they are otherwise limited in specific instances), either individually or as part of a larger group. It will be understood that "substitution" or "substituted by" or "substituted with" includes the implicit proviso that such substitution is in accordance with the permitted valence of the substituted atom and the substituent, as well as represents a stable compound, which does not readily undergo transformation such as by rearrangement, cyclization, elimination, etc.

The term "alkyl" whether used alone or as part of a substituent group, refers to the radical of saturated aliphatic groups, including straight or branched-chain containing from 1 to 10 carbon atoms. Furthermore, unless stated otherwise, the term "alkyl" includes unsubstituted as well as substituted alkyl. Suitable alkyl residues contain from 1 to 6 carbon atoms, for example, from 1 to 4 carbon atoms, such as methyl, ethyl, propyl, isopropyl, n-butyl, isobutyl and t-butyl.

The term "lower alkyl" whether used alone or as part of a substituent group, refers to the radical of saturated aliphatic groups, including straight or branched-chain containing from one to six carbon atoms, such as methyl, ethyl, n-propyl, isopropyl, n-butyl, sec-butyl, isobutyl, tert-butyl, n-pentyl and n-hexyl. Unless stated otherwise, alkyl groups can be unsubstituted or substituted by one or more identical or different substituents. Any kind of substituent present in substituted alkyl residues can be present in any desired position provided that the substitution does not lead to an unstable molecule. A substituted alkyl refers to an alkyl residue in which one or more hydrogen atoms are replaced with substituents, for example, halogen, hydroxy, carbonyl, carboxy, alkoxy, cycloalkyl, ester, ether, cyano, amino, —$CONH_2$, imino, alkylthio, thioester, sulfonyl, nitro, haloalkyl, aralkyl, acyl, acyloxy, aryl, heterocyclyl, heteroaryl, —$NR_xCOR_y$, —$NR_xSOR_y$, —$NR_xSO_2R_y$, —$S(O)_nR_x$, —$S(O)_mNR_xR_y$, wherein $R_x$ and $R_y$ are independently selected from hydrogen, hydroxy, alkyl, alkoxy, alkenyl, alkynyl, cycloalkyl, aryl, aralkyl and heterocyclyl; n is 0, 1 or 2 and m is 1 or 2.

The term "alkenyl" refers to an unsaturated, branched, straight chain or cyclic alkyl group having from 2 to 6 carbon atoms and at least one carbon-carbon double bond (two adjacent $sp^2$ carbon atoms). Depending on the placement of double bond and substituents if any, the geometry of the double bond may be entgegen (E), or zusammen (Z), cis or trans. Examples of alkenyl include, but are not limited to vinyl, allyl and 2-propenyl. Unless stated otherwise, the alkenyl groups can be unsubstituted or substituted by one or more of the same or different groups such as halogen, amino, cyano, nitro, hydroxy, carboxy, acyl, acetoxy, alkyl, haloalkyl, alkoxy, cycloalkyl, aryloxy, aryl, aralkyl or heterocyclyl.

The term "alkynyl" refers to an unsaturated, branched or straight chain having from 2 to 6 carbon atoms and at least one carbon-carbon triple bond (two adjacent sp carbon atoms). Examples of alkynyl include, but are not limited to, ethynyl, 1-propynyl, 3-propynyl and 3-butynyl. Unless stated otherwise, the alkynyl groups can be unsubstituted or substituted with one or more groups, such as halogen, hydroxy, carboxy, amino, cyano, nitro, acyl, acetoxy, alkyl, haloalkyl, cycloalkyl, alkoxy, aryloxy, aryl, aralkyl or heterocyclyl.

The term "cycloalkyl" refers to a saturated or partially unsaturated cyclic hydrocarbon group including 1, 2 or 3 rings and including a total of 3 to 14 carbons forming the rings. Suitable examples of cycloalkyl include cyclopropyl, cyclobutyl, cyclopentyl, cyclohexyl and cyclooctyl. Unless stated otherwise, the cycloalkyl groups can be unsubstituted or substituted with one or more of the same or different groups, such as halogen, hydroxy, alkoxy, oxo, alkyl, cycloalkyl, carboxy, acyl, acyloxy, amino, cyano, nitro, carbonyl, ester, ether, —$CONH_2$, imino, alkylthio, aryl or heterocyclyl.

The term "alkoxy" refers to the alkyl-O— wherein the term alkyl is as defined above. Examples of alkoxy include, but are not limited to methoxy and ethoxy.

The term "haloalkyl" as used herein refers to radicals wherein any one or more of the alkyl carbon atoms are substituted with one or more halogen. Examples of haloalkyl include, but are not limited to trifluoromethyl and trichloromethyl. Specifically embraced are monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "perfluoroalkyl" means alkyl radicals having all hydrogen atoms replaced with fluoro atoms. Examples include trifluoromethyl and pentafluoroethyl.

The term "haloalkoxy" as used herein refers to a haloalkyl group attached to the parent molecular moiety through an oxygen atom.

The term "acyl" refers to the group —C(O)$R_a$, wherein $R_a$ is alkyl, cycloalkyl, aryl, aralkyl, heteroaryl and heteroaralkyl. The groups alkyl, cycloalkyl, aryl, aralkyl, heteroaryl and heteroaralkyl can be unsubstituted or substituted with halogen, hydroxy, carboxy, alkoxy, cycloalkyl, ester, ether, cyano, amino, —$CONH_2$, alkylthio, thioester, sulfonyl, nitro, haloalkyl, —$NR_xCOR_y$, —$NR_xSOR_y$, —$NR_xSO_2R_y$, —$S(O)_nR_x$, —$S(O)_mNR_xR_y$, wherein $R_x$ and $R_y$ are independently selected from hydrogen, hydroxy, alkyl, alkoxy, alkenyl, alkynyl, cycloalkyl, aryl, aralkyl and heterocyclyl; n is as an integer from 0-2 and m is an integer from 1 to 2.

The term "ester" refers to a group of the form —$COOR_a$, wherein $R_a$ is alkyl and aralkyl as defined above. Examples include the physiologically hydrolysable esters such as the methyl, ethyl, n- and iso-propyl, n-, sec- and tert-butyl and benzyl esters.

The term "ether" refers to a group of formula —$R_aOR_a$, wherein $R_a$ is independently selected from alkyl, cycloalkyl, aryl, aralkyl, heteroaryl and heterocyclyl as defined above.

The term "aryl" refers to a monocyclic or polycyclic hydrocarbon group having up to 10 ring carbon atoms, in which at least one carbocyclic ring is present that has a conjugated π electron system. Examples of aryl residues include phenyl and naphthyl. Unless stated otherwise, aryl residues, for example phenyl or naphthyl, can be unsubstituted or substituted by one or more substituents, for example, up to five identical or different substituents selected from the group consisting of alkyl, haloalkyl, acyl, halogen, hydroxy, alkoxy, haloalkoxy, trifluoromethoxy, aryloxy, amino, cyano, nitro, thiol, —$CONH_2$, carbonyl, sulfonyl and aryl.

Aryl residues can be bonded via any desired position, and in substituted aryl residues, the substituents can be located in any desired position. For example, in monosubstituted phenyl residues the substituent can be located in the 2-position, the 3-position, the 4-position, the 5-position, or the 6-position. If the phenyl group carries two substituents, they can be located in 2,3-position, 2,4-position, 2,5-position, 2,6-position, 3,4-position or 3,5-position.

The term "aryloxy" refers to the aryl-O— wherein the term aryl is as defined above. Exemplary aryloxy groups include, but are not limited to, phenoxy and naphthoxy.

The terms "heterocyclyl" and "heterocyclic" refer to a saturated, partially unsaturated or aromatic monocyclic or polycyclic ring system containing 3-14 ring atoms of which 1, 2, 3 or 4 are identical or different heteroatoms selected from nitrogen, oxygen and sulfur. The heterocyclyl group may, for example, have at least one heteroatom selected from 0 to 2 oxygen atoms, 0 to 2 sulfur atoms and 0 to 4 nitrogen atoms in the ring. Monocyclic heterocyclyl groups include 3-membered, 4-membered, 5-membered, 6-membered and 7-membered rings. Suitable examples of heterocyclyl include, but are not limited to, pyrrolyl, imidazolyl, thiophenyl, pyrrolidinyl, pyridinyl, pyrazinyl, pyridazinyl, pyrimidinyl, pyrazolyl, triazolyl, tetrazolyl, piperidinyl, piperazinyl and morpholinyl. Polycyclic heterocyclyl groups can include two fused rings (bicyclic) or three fused rings (tricyclic), one of which is a 5-, 6- or 7-membered heterocyclic ring and the other is a 5-, 6- or 7-membered carbocyclic or heterocyclic ring. Exemplary bicyclic heterocyclic groups include benzoxazolyl, quinolinyl, isoquinolyl, indolyl, isoindolyl, and benzofurazanyl. Exemplary tricyclic heterocyclic groups include, but not limited to, substituted or unsubstituted naphthofuranyl, benzoindole, pyrroloquinoline and furoquinoline. Heterocyclyl includes saturated heterocyclic ring systems, which do not contain any double bonds within the rings, as well as unsaturated heterocyclic ring systems, which contain one or more, up to 5 double bonds within the rings provided that the resulting system is stable. Unsaturated rings may be non-aromatic or aromatic.

Aromatic heterocyclyl groups may also be referred to by the customary term "heteroaryl" for which all the definitions and explanations above and below relating to heterocyclyl apply. Unless stated otherwise, the heteroaryl and heterocyclyl group can be unsubstituted or substituted with one or more (e.g., up to 5), identical or different, substituents. Examples of substituents for the ring carbon and ring nitrogen atoms are alkyl, acyl, alkoxy, trifluoromethoxy, halogen, hydroxy, hydroxyalkyl, haloalkyl, aryloxy, amino, cyano, nitro, thiol, —$CONH_2$, carbonyl, carboxy, sulfonyl, cycloalkyl, heterocyclyl, aryl and —$NHR_8$, wherein $R_8$ is alkyl, alkenyl, alkynyl, cycloalkyl, aralkyl, aryl, heteroaryl or heterocyclyl. The substituents can be present at one or more positions provided that it results into a stable molecule.

The term "aralkyl" refers to an alkyl group substituted with an aryl or heteroaryl group, wherein the terms alkyl, aryl and heteroaryl are as defined above. Exemplary aralkyl groups include —$(CH_2)_p$-phenyl, —$(CH_2)_p$-pyridyl, wherein p is an integer from 1 to 6. The alkyl, aryl and heteroaryl in the said aralkyl group are as defined above.

The term "heteroatom" refers to nitrogen, oxygen and sulfur. It should be noted that any heteroatom with unsatisfied valences is assumed to have a hydrogen atom to satisfy the valences. The ring heteroatoms can be present in any desired number and in any position with respect to each other provided that the resulting heterocyclic system is stable and suitable as a subgroup in a drug substance.

The term "halo" or "halogen" unless otherwise stated refers to fluorine, chlorine, bromine, or iodine atom.

The term "amino" refers to the group —$NH_2$ which may be optionally substituted with alkyl, alkenyl, alkynyl, aryl, heterocyclyl, or cycloalkyl wherein the terms alkyl, alkenyl, alkynyl, aryl, heterocyclyl and cycloalkyl are as defined herein above.

As used herein, the terms "treat" and "therapy" and the like refer to alleviate, slow the progression, prophylaxis, modulation, attenuation or cure of existing disease (e.g., cancer or inflammation).

Embodiments

In an embodiment, the present invention provides compounds of formula (I), wherein, $R_1$ is phenyl, which is unsubstituted or substituted with an alkyl group, wherein the alkyl group is unsubstituted or substituted with one or more of the same or different groups selected from nitro, cyano, —$CONH_2$, amino, halogen, hydroxy, haloalkyl and alkoxy;

$R_2$ is alkyl, alkenyl, alkynyl, cycloalkyl, aryl, heteroaryl, heterocyclyl, amino, —$NHR_8$ or $NR_8R_8$;

$R_3$, $R_4$, $R_5$ and $R_7$ are each independently hydrogen, alkyl, alkenyl, alkynyl, cycloalkyl, aralkyl, halogen, acyl, hydroxy, alkoxy, amino, cyano and nitro;

$R_6$ is hydrogen, alkyl, alkenyl, alkynyl, cycloalkyl, aralkyl, halogen, acyl, hydroxy, amino, cyano, nitro, thiol, —COOH, —$CONH_2$, —$OR_8$, —$NHR_8$, —$SR_8$ or —$B(OH)_2$;

each $R_8$ is independently selected from alkyl, alkenyl, alkynyl, cycloalkyl, aralkyl, aryl, heteroaryl or heterocyclyl; and Y is —C(O), —C(S) or —S(O)$_n$; wherein n is 0, for 2;

wherein alkyl is unsubstituted or substituted with one or more of the same or different groups such as cyano, nitro, halogen, hydroxy, amino, —CONH$_2$, alkoxy, acyl and aryl;

alkenyl is unsubstituted or substituted by one or more of the same or different groups such as cyano, nitro, halogen, lower alkyl, haloalkyl, hydroxy, alkoxy, acyl and aryl;

alkynyl is unsubstituted or substituted with one or more of the same or different groups selected from cyano, nitro, halogen, lower alkyl, haloalkyl, hydroxy, alkoxy, acyl and aryl;

cycloalkyl is unsubstituted or substituted with one or more of the same or different groups such as cyano, nitro, halogen, hydroxy, amino, —CONH$_2$, lower alkyl, haloalkyl, alkoxy, acyl and aryl;

aryl is unsubstituted or substituted with one or more of the same or different groups selected from cyano, nitro, halogen, lower alkyl, haloalkyl, hydroxy, alkoxy and acyl;

heteroaryl is unsubstituted or substituted with one or more of the same or different groups selected from cyano, nitro, lower alkyl, haloalkyl, alkoxy, hydroxy, halogen, amino, —CONH$_2$, carboxy and acyl;

heterocyclyl is unsubstituted or substituted with one or more of the same or different groups selected from cyano, nitro, halogen, lower alkyl, haloalkyl, hydroxy, alkoxy, amino, —CONH$_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein, $R_1$ is phenyl substituted with —C(CH$_3$)$_2$CN;

$R_2$ is alkyl, alkenyl, alkynyl, cycloalkyl, aryl, heteroaryl, heterocyclyl, amino, —NHR$_8$ or —NR$_8$R$_8$;

$R_3$, $R_4$, $R_5$ and $R_7$ are each independently selected from hydrogen, alkyl, alkenyl, alkynyl, cycloalkyl, aralkyl, halogen, acyl, hydroxy, alkoxy, amino, cyano and nitro;

$R_6$ is hydrogen, alkyl, alkenyl, alkynyl, cycloalkyl, aralkyl, halogen, acyl, hydroxy, amino, cyano, nitro, thiol, —COOH, —CONH$_2$, —OR$_8$, —NHR$_8$, —SR$_8$ or —B(OH)$_2$;

each $R_8$ is independently selected from alkyl, alkenyl, alkynyl, cycloalkyl, aralkyl, aryl, heteroaryl or heterocyclyl; and Y is —C(O), —C(S) or —S(O)$_n$, wherein n is 0, 1 or 2;

wherein, alkyl is unsubstituted or substituted with one or more of the same or different groups selected from cyano, nitro, halogen, amino, —CONH$_2$, hydroxy, alkoxy, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, halogen, amino, —CONH$_2$, hydroxy, lower alkyl, haloalkyl, alkoxy, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —CONH$_2$, carboxy, acyl and aryl;

heterocyclyl is unsubstituted or substituted with one or more of the same or different groups selected from cyano, nitro, halogen, lower alkyl, haloalkyl, hydroxy, alkoxy, amino, —CONH$_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein, $R_1$ is phenyl substituted with —C(CH$_3$)$_2$CN;

$R_2$ is alkyl, alkenyl, alkynyl, cycloalkyl, aryl, heteroaryl, heterocyclyl, amino, —NHR$_8$ or —NR$_8$R$_8$;

$R_3$, $R_4$, $R_5$ and $R_7$ are each independently selected from hydrogen, alkyl, alkenyl, alkynyl, cycloalkyl, aralkyl, halogen, acyl, hydroxy, alkoxy, amino, cyano and nitro;

$R_6$ is halogen or lower alkyl;

each $R_8$ is independently selected from alkyl, alkenyl, alkynyl, cycloalkyl, aralkyl, aryl, heteroaryl or heterocyclyl; and Y is —C(O), —C(S) or —S(O)$_2$;

wherein, alkyl is unsubstituted or substituted with one or more of the same or different groups selected from cyano, nitro, halogen, amino, —CONH$_2$, hydroxy, alkoxy, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, halogen, amino, —CONH$_2$, hydroxy, lower alkyl, haloalkyl, alkoxy, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —CONH$_2$, carboxy, acyl and aryl;

heterocyclyl is unsubstituted or substituted with one or more of the same or different groups selected from cyano, nitro, halogen, lower alkyl, haloalkyl, hydroxy, alkoxy, amino, —CONH$_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein, $R_1$ is phenyl substituted with —C(CH$_3$)$_2$CN;

$R_2$ is alkyl, alkenyl, alkynyl, cycloalkyl, aryl, heteroaryl, heterocyclyl, amino, —NHR$_8$ or —NR$_8$R$_8$;

$R_3$, $R_4$, $R_5$ and $R_7$ are hydrogen;

$R_6$ is halogen or lower alkyl;

each $R_8$ is independently selected from alkyl, alkenyl, alkynyl, cycloalkyl, aralkyl, aryl, heteroaryl or heterocyclyl; and Y is —C(O), —C(S) or —S(O)$_2$;

wherein, alkyl is unsubstituted or substituted with one or more of the same or different groups selected from cyano, nitro, amino, —CONH$_2$, hydroxy, alkoxy, halogen, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, amino, —$CONH_2$, hydroxy, alkoxy, halogen, lower alkyl, haloalkyl, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

heterocyclyl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein,
$R_1$ is phenyl substituted with —$C(CH_3)_2CN$;
$R_2$ is alkyl, alkenyl, alkynyl, cycloalkyl, aryl, heteroaryl, heterocyclyl, amino, —$NHR_8$ or —$NR_8R_8$;
$R_3$, $R_4$, $R_5$ and $R_7$ are each independently hydrogen;
$R_6$ is halogen or lower alkyl;
each $R_8$ is independently selected from alkyl, alkenyl, alkynyl, cycloalkyl, aralkyl, aryl, heteroaryl or heterocyclyl; and
Y is —$S(O)_2$;
wherein, alkyl is unsubstituted or substituted with one or more of the same or different groups selected from cyano, nitro, halogen, amino, —$CONH_2$, hydroxy, alkoxy, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, halogen, amino, —$CONH_2$, hydroxy, lower alkyl, haloalkyl, alkoxy, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

heterocyclyl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein,
$R_1$ is phenyl substituted with —$C(CH_3)_2CN$;
$R_2$ is alkyl, aryl, or heteroaryl;
$R_3$, $R_4$, $R_5$ and $R_7$ are each independently hydrogen;
$R_6$ is halogen or lower alkyl; and
Y is —$S(O)_2$;
wherein, alkyl is unsubstituted or substituted with one or more of the same or different groups selected from cyano, nitro, halogen, amino, —$CONH_2$, hydroxy, alkoxy, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein,
$R_1$ is phenyl substituted with —$C(CH_3)_2CN$;
$R_2$ is alkyl, alkenyl, alkynyl, cycloalkyl, aryl, heteroaryl, heterocyclyl, amino, —$NHR_8$ or —$NR_8R_8$;
$R_3$, $R_4$, $R_5$ and $R_7$ are each independently hydrogen;
$R_6$ is halogen or lower alkyl;
each $R_8$ is independently selected from alkyl, alkenyl, alkynyl, cycloalkyl, aralkyl, aryl, heteroaryl or heterocyclyl; and
Y is —$C(O)$;
wherein, alkyl is unsubstituted or substituted with one or more of the same or different groups selected from cyano, nitro, amino, —$CONH_2$, hydroxy, alkoxy, halogen, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, amino, —$CONH_2$, hydroxy, alkoxy, halogen, lower alkyl, haloalkyl, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

heterocyclyl is unsubstituted or substituted with one or more of the same or different groups selected from cyano, nitro, halogen, lower alkyl, haloalkyl, hydroxy, alkoxy, amino, —$CONH_2$, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein,
$R_1$ is phenyl substituted with —$C(CH_3)_2CN$;
$R_2$ is alkyl, alkenyl, aryl, heteroaryl, heterocyclyl or —$NHR_8$;
$R_3$, $R_4$, $R_5$ and $R_7$ are each independently hydrogen;
$R_6$ is halogen or lower alkyl;

R₈ is alkyl, alkenyl, alkynyl, cycloalkyl, aralkyl, aryl, heteroaryl or heterocyclyl; and Y is —C(O);

wherein, alkyl is unsubstituted or substituted with one or more of the same or different groups selected from cyano, nitro, amino, —CONH₂, hydroxy, alkoxy, halogen, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, amino, —CONH₂, hydroxy, alkoxy, halogen, lower alkyl, haloalkyl, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —CONH₂, carboxy, acyl and aryl;

heterocyclyl is unsubstituted or substituted with one or more of the same or different groups selected from cyano, nitro, halogen, lower alkyl, haloalkyl, hydroxy, alkoxy, amino, —CONH₂, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein, $R_1$ is phenyl substituted with —C(CH₃)₂CN;

$R_2$ is alkyl, alkenyl, aryl, heterocyclyl or —NHR₈;

$R_3$, $R_4$, $R_5$ and $R_7$ are each independently hydrogen;

$R_6$ is halogen or lower alkyl;

$R_8$ is alkyl, alkenyl, aralkyl or aryl; and

Y is —C(O);

wherein, alkyl is unsubstituted or substituted with one or more of the same or different groups selected from cyano, nitro, amino, —CONH₂, hydroxy, alkoxy, halogen, acyl and aryl;

alkenyl is unsubstituted or substituted with one or more of the same or different groups selected from cyano, nitro, halogen, lower alkyl, haloalkyl, hydroxy, alkoxy, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heterocyclyl is unsubstituted or substituted with one or more of the same or different groups selected from cyano, nitro, halogen, lower alkyl, haloalkyl, hydroxy, alkoxy, amino, —CONH₂, carboxy, acyl and aryl;

in all their stereoisomeric and tautomeric forms and mixtures thereof in all ratios, their pharmaceutically acceptable salts and pharmaceutically acceptable solvates.

In another embodiment, the present invention provides compounds of formula (I), wherein, $R_1$ is phenyl substituted with —C(CH₃)₂CN;

$R_2$ is —NHR₈;

$R_3$, $R_4$, $R_5$ and $R_7$ are each independently hydrogen;

$R_6$ is halogen or lower alkyl;

$R_8$ is alkyl, alkenyl, alkynyl, cycloalkyl, aralkyl, aryl, heteroaryl or heterocyclyl; and Y is —C(S);

wherein, alkyl is unsubstituted or substituted with one or more of the same or different groups selected from cyano, nitro, amino, —CONH₂, hydroxy, alkoxy, halogen, acyl and aryl;

alkenyl is unsubstituted or substituted with one or more of the same or different groups selected from cyano, nitro, halogen, lower alkyl, haloalkyl, hydroxy, alkoxy, acyl and aryl;

alkynyl is unsubstituted or substituted by one or more of the same or different groups selected from cyano, nitro, halogen, lower alkyl, haloalkyl, hydroxy, alkoxy, acyl and aryl;

cycloalkyl is unsubstituted or substituted with one or more of the same or different groups selected from cyano, nitro, amino, —CONH₂, hydroxy, alkoxy, halogen, lower alkyl, haloalkyl, acyl and aryl;

aryl is unsubstituted or substituted with one or more of the same or different groups selected from cyano, nitro, halogen, lower alkyl, haloalkyl, hydroxy, alkoxy, haloalkoxy, acyl and aryl;

heteroaryl is unsubstituted or substituted with one or more of the same or different groups selected from cyano, nitro, halogen, lower alkyl, haloalkyl, hydroxy, alkoxy, amino, —CONH₂, carboxy, acyl and aryl;

heterocyclyl is unsubstituted or substituted with one or more of the same or different groups selected from cyano, nitro, halogen, lower alkyl, haloalkyl, hydroxy, alkoxy, amino, —CONH₂, carboxy, acyl and aryl;

in all their stereoisomeric and tautomeric forms and mixtures thereof in all ratios, their pharmaceutically acceptable salts and pharmaceutically acceptable solvates.

Representative compounds, encompassed in accordance with the present invention include:

2-(4-(8-bromo-2-oxo-3-(4-(trifluoromethoxy)phenylsulfonyl)-2,3-dihydro-1H-imidazo[4,5-c]quinolin-1-yl)phenyl)-2-methylpropanenitrile;

2-(8-bromo-1-(4-(2-cyanopropan-2-yl)phenyl)-2-oxo-1H-imidazo[4,5-c]quinolin-3 (2H)-ylsulfonyl)benzonitrile;

2-(4-(8-bromo-2-oxo-3-(m-tolylsulfonyl)-2,3-dihydro-1H-imidazo[4,5-c]quinolin-1-yl)phenyl)-2-methylpropanenitrile;

2-(4-(8-bromo-3-(2-methyl-4-nitrophenylsulfonyl)-2-oxo-2,3-dihydro-1H-imidazo[4,5-c]quinolin-1-yl)phenyl)-2-methylpropanenitrile;

2-(4-(8-bromo-3-(3-fluoro-4-methylphenylsulfonyl)-2-oxo-2,3-dihydro-1H-imidazo[4,5-c]quinolin-1-yl)phenyl)-2-methylpropanenitrile;

2-(4-(8-bromo-3-(3,5-dimethylphenylsulfonyl)-2-oxo-2,3-dihydro-1H-imidazo[4,5-c]quinolin-1-yl)phenyl)-2-methylpropanenitrile;

2-(4-(8-bromo-2-oxo-3-(phenylsulfonyl)-2,3-dihydro-1H-imidazo[4,5-c]quinolin-1-yl)phenyl)-2-methylpropanenitrile;

2-(4-(8-bromo-2-oxo-3-tosyl-2,3-dihydro-1H-imidazo[4,5-c]quinolin-1-yl)phenyl)-2-methylpropanenitrile;

2-(4-(8-bromo-2-oxo-3-(thiophen-2-ylsulfonyl)-2,3-dihydro-1H-imidazo[4,5-c]quinolin-1-yl)phenyl)-2-methylpropanenitrile;

2-(4-(8-bromo-3-(3-fluorophenylsulfonyl)-2-oxo-2,3-dihydro-1H-imidazo[4,5-c]quinolin-1-yl)phenyl)-2-methylpropanenitrile;

2-(4-(8-bromo-2-oxo-3-(quinolin-8-ylsulfonyl)-2,3-dihydro-1H-imidazo[4,5-c]quinolin-1-yl)phenyl)-2-methylpropanenitrile;

2-(4-(3-(4-acetylphenylsulfonyl)-8-bromo-2-oxo-2,3-dihydro-1H-imidazo[4,5-c]quinolin-1-yl)phenyl)-2-methylpropanenitrile;

2-(4-(8-bromo-2-oxo-3-(3-(trifluoromethyl)phenylsulfonyl)-2,3-dihydro-1H-imidazo[4,5-c]quinolin-1-yl)phenyl)-2-methylpropanenitrile;
2-(4-(8-bromo-3-(3-methoxyphenylsulfonyl)-2-oxo-2,3-dihydro-1H-imidazo[4,5-c]quinolin-1-yl)phenyl)-2-methylpropanenitrile;
2-(4-(8-bromo-3-(3-bromophenylsulfonyl)-2-oxo-2,3-dihydro-1H-imidazo[4,5-c]quinolin-1-yl)phenyl)-2-methylpropanenitrile;
2-(4-(8-bromo-3-(3,5-difluorophenylsulfonyl)-2-oxo-2,3-dihydro-1H-imidazo[4,5-c]quinolin-1-yl)phenyl)-2-methylpropanenitrile;
2-(4-(8-bromo-3-(2,4-difluorophenylsulfonyl)-2-oxo-2,3-dihydro-1H-imidazo[4,5-c]quinolin-1-yl)phenyl)-2-methylpropanenitrile;
2-(4-(8-bromo-3-(methylsulfonyl)-2-oxo-2,3-dihydro-1H-imidazo[4,5-c]quinolin-1-yl)phenyl)-2-methylpropanenitrile;
2-(4-(8-chloro-2-oxo-3-(m-tolylsulfonyl)-2,3-dihydro-1H-imidazo[4,5-c]quinolin-1-yl)phenyl)-2-methylpropanenitrile;
2-(8-chloro-1-(4-(2-cyanopropan-2-yl)phenyl)-2-oxo-1H-imidazo[4,5-c]quinolin-3(2H)-ylsulfonyl)benzonitrile;
2-methyl-2-(4-(8-methyl-2-oxo-3-(m-tolylsulfonyl)-2,3-dihydro-1H-imidazo[4,5-c]quinolin-1-yl)phenyl)propanenitrile;
2-(4-(3-(3-fluorophenylsulfonyl)-8-methyl-2-oxo-2,3-dihydro-1H-imidazo[4,5-c]quinolin-1-yl)phenyl)-2-methylpropanenitrile;
2-methyl-2-(4-(8-methyl-3-(2-methyl-5-nitrophenylsulfonyl)-2-oxo-2,3-dihydro-1H-imidazo[4,5-c]quinolin-1-yl)phenyl)propanenitrile;
2-methyl-2-(4-(8-methyl-2-oxo-3-(quinolin-8-ylsulfonyl)-2,3-dihydro-1H-imidazo[4,5-c]quinolin-1-yl)phenyl)propanenitrile;
2-(4-(3-(4-acetylphenylsulfonyl)-8-methyl-2-oxo-2,3-dihydro-1H-imidazo[4,5-c]quinolin-1-yl)phenyl)-2-methylpropanenitrile;
2-(4-(8-bromo-3-(morpholine-4-carbonyl)-2-oxo-2,3-dihydro-1H-imidazo[4,5-c]quinolin-1-yl)phenyl)-2-methylpropanenitrile;
(E)-2-(4-(8-bromo-3-but-2-enoyl-2-oxo-2,3-dihydro-1H-imidazo[4,5-c]quinolin-1-yl)phenyl)-2-methylpropanenitrile;
2-(4-(8-bromo-2-oxo-3-(2-propylpentanoyl)-2,3-dihydro-1H-imidazo[4,5-c]quinolin-1-yl)phenyl)-2-methylpropanenitrile;
(E)-2-(4-(8-bromo-3-cinnamoyl-2-oxo-2,3-dihydro-1H-imidazo[4,5-c]quinolin-1-yl)phenyl)-2-methylpropanenitrile;
2-(4-(3-benzoyl-8-bromo-2-oxo-2,3-dihydro-1H-imidazo[4,5-c]quinolin-1-yl)phenyl)-2-methylpropanenitrile;
8-bromo-1-(4-(2-cyanopropan-2-yl)phenyl)-N-(4-methoxyphenyl)-2-oxo-1H-imidazo[4,5-c]quinoline-3(2H)-carboxamide;
N-benzyl-8-bromo-1-(4-(2-cyanopropan-2-yl)phenyl)-2-oxo-1H-imidazo[4,5-c]quinoline-3(2H)-carboxamide;
8-Bromo-N-(2-bromophenyl)-1-(4-(2-cyanopropan-2-yl)phenyl)-2-oxo-1H-imidazo[4,5-c]quinoline-3(2H)-carboxamide;
8-bromo-N-(2-chloroethyl)-1-(4-(2-cyanopropan-2-yl)phenyl)-2-oxo-1H-imidazo[4,5-c]quinoline-3(2H)-carboxamide;
N-allyl-8-bromo-1-(4-(2-cyanopropan-2-yl)phenyl)-2-oxo-1H-imidazo[4,5-c]quinoline-3(2H)-carboxamide;
2-(4-(3-acetyl-8-chloro-2-oxo-2,3-dihydro-1H-imidazo[4,5-c]quinolin-1-yl)phenyl)-2-methylpropanenitrile;
2-(4-(3-benzoyl-8-chloro-2-oxo-2,3-dihydro-1H-imidazo[4,5-c]quinolin-1-yl)phenyl)-2-methylpropanenitrile;
(E)-2-(4-(3-but-2-enoyl-8-chloro-2-oxo-2,3-dihydro-1H-imidazo[4,5-c]quinolin-1-yl)phenyl)-2-methylpropanenitrile;
(E)-2-(4-(3-but-2-enoyl-8-methyl-2-oxo-2,3-dihydro-1H-imidazo[4,5-c]quinolin-1-yl)phenyl)-2-methylpropanenitrile;
8-bromo-N-(2-chloroethyl)-1-(4-(2-cyanopropan-2-yl)phenyl)-2-oxo-1H-imidazo[4,5-c]quinoline-3(2H)-carbothioamide;

and their pharmaceutically acceptable salts and solvates.

According to a further feature of the present invention there is provided a process for the preparation of the compounds of the present invention as given in the following scheme.

According to a further aspect of the present invention, there is provided a process for the preparation of a compound of formula (A 8),

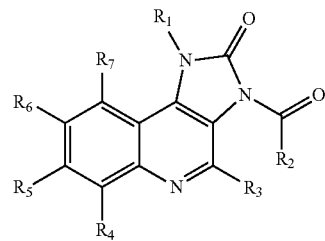

(A 8)

wherein, $R_2$ is alkyl, alkenyl, alkynyl, cycloalkyl, aryl, heterocyclyl or heteroaryl; $R_3$ is hydrogen; $R_1$, $R_4$, $R_5$, $R_6$ and $R_7$ are as defined for formula (I), which comprises, reacting a compound of formula (A 7)

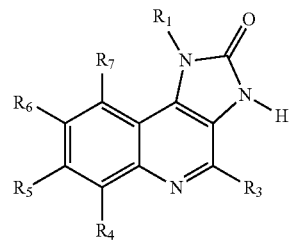

(A 7)

with compound of formula $R_2COCl$, wherein $R_2$ is alkyl, alkenyl, alkynyl, cycloalkyl, aryl, heterocyclyl or heteroaryl; $R_3$ is hydrogen; $R_1$, $R_4$, $R_5$, $R_6$ and $R_7$ are as defined for formula (I), in the presence of a base such as sodium hydride and solvent such as DMF; and optionally converting the resulting compound into a pharmaceutically acceptable salt.

According to a further aspect of the present invention, there is provided a process for the preparation of a compound of formula (A 9),

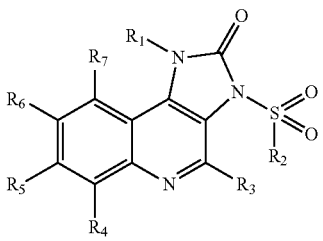

(A 9)

wherein, $R_3$ is hydrogen; $R_1$, $R_2$, $R_4$, $R_5$, $R_6$ and $R_7$ are as defined for formula (I), which comprises, reacting a compound of formula (A 7)

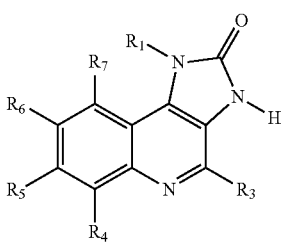

(A 7)

with compound of formula $R_2SO_2Cl$, wherein $R_3$ is hydrogen; $R_1$, $R_2$, $R_4$, $R_5$, $R_6$ and $R_7$ are as defined for formula (I), in the presence of a base such as triethylamine; and optionally converting the resulting compound into a pharmaceutically acceptable salt.

According to a further aspect of the present invention, there is provided a process for the preparation of a compound of formula (A 10),

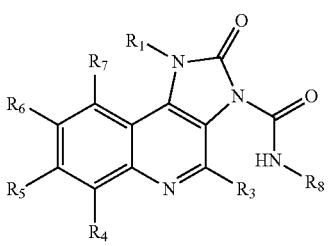

(A 10)

wherein, $R_3$ is hydrogen; $R_1$, $R_4$, $R_5$, $R_6$, $R_7$ and $R_8$ are as defined for formula (I), which comprises, reacting a compound of formula (A 7)

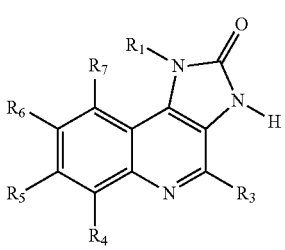

(A 7)

with compound of formula $R_8N=C=O$, wherein $R_3$ is hydrogen; $R_1$, $R_4$, $R_5$, $R_6$, $R_7$ and $R_8$ are as defined for formula (I), in the presence of a solvent such as benzene or DCM;

optionally converting the resulting compound into a pharmaceutically acceptable salt.

According to a further aspect of the present invention, there is provided a process for the preparation of a compound of formula (A 11),

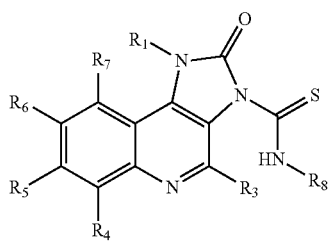

(A 11)

wherein, $R_3$ is hydrogen; $R_1$, $R_4$, $R_5$, $R_6$, $R_7$ and $R_8$ are as defined for formula (I), which comprises, reacting a compound of formula (A 7)

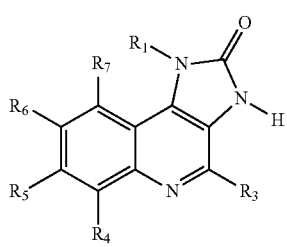

(A 7)

with compound of formula $R_8N=C=S$, wherein $R_3$ is hydrogen; $R_1$, $R_4$, $R_5$, $R_6$, $R_7$ and $R_8$ are as defined for formula (I), in the presence of a solvent such as DCM; and optionally converting the resulting compound into a pharmaceutically acceptable salt.

Schemes

The compounds of the present invention also include all stereoisomeric forms and mixtures thereof in all ratios and their pharmaceutically acceptable salts, solvates and polymorphs. Furthermore, all the compounds of the present invention are a subject of the present invention in the form of their prodrugs and other derivatives.

According to another aspect of the present invention, the compounds of formula (I) can be prepared in a number of ways using methods well known to the person skilled in the art. Examples of methods to prepare the present compounds are described below and illustrated in Scheme 1 but not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention, are referred to with general formulae namely (A 1), (A 2), (A 3), (A 4), (A 5), (A 6) and (A 7). The compounds of the present invention are referred to with general formulae namely (A 8), (A 9), (A 10) and (A 11).

The process used in scheme 1 of the present invention, is referred to with general symbols namely 1a, 1b, 1c, 1d, 1e, 1f, 1g, 1 h, 1i and 1j.

Process for the preparation of compounds of the present invention is set forth in the following scheme:

SCHEME 1

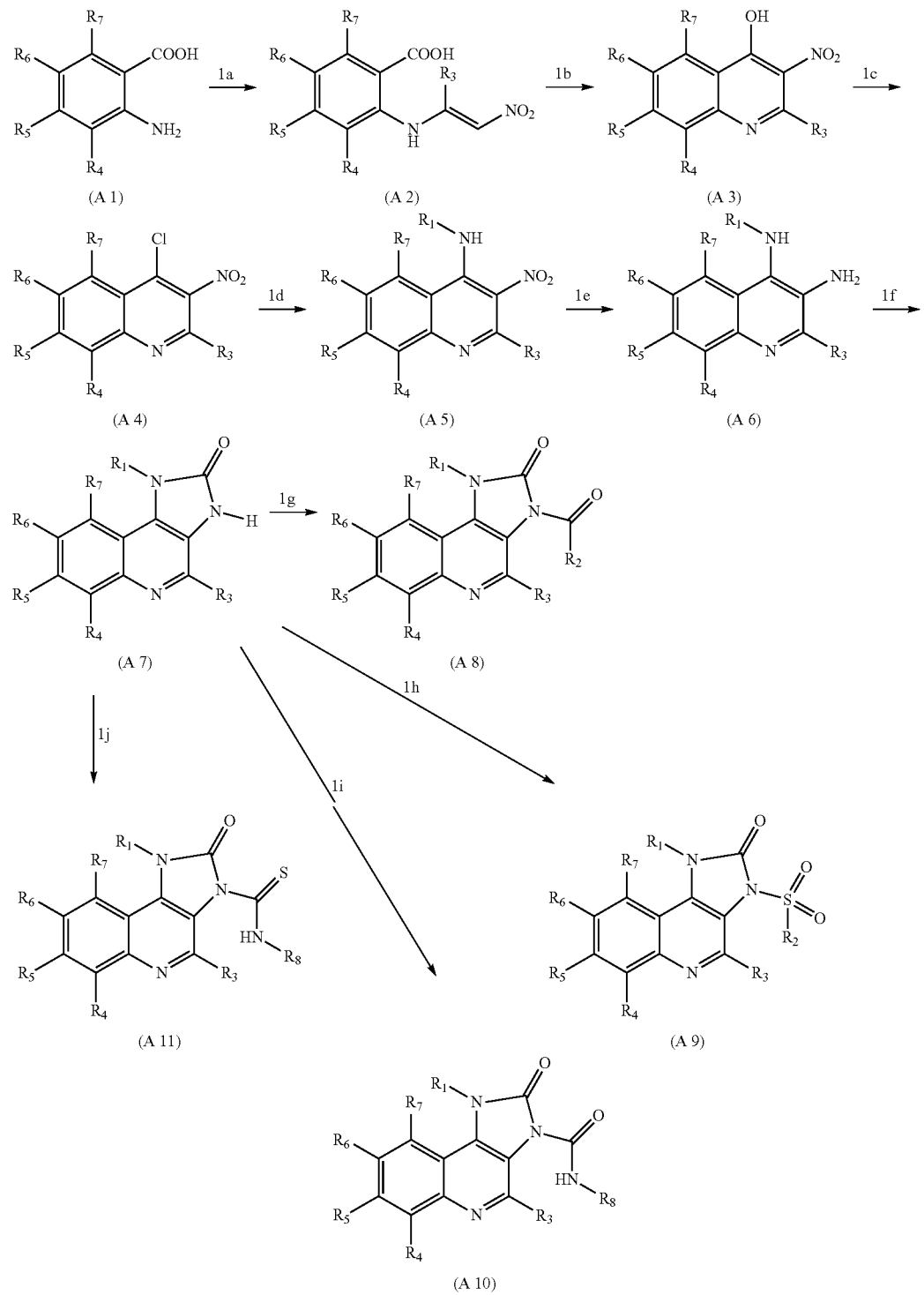

wherein $R_3$ is hydrogen; $R_1$, $R_2$, $R_4$, $R_5$, $R_6$, $R_7$ and $R_8$ are as defined for formula (I).

Reaction Conditions

1a: conc. HCl, water, NaOH, ice, $CH_3NO_2$;
1b: Acetic anhydride, potassium acetate, 125° C.;
1c: $POCl_3$, 125° C.;
1d: $R_1$—$NH_2$, acetic acid, room temperature;
1e: 10% Pd/C or Raney Ni; $H_2$; MeOH or MeOH:THF (1:1), room temperature;
1f: Triphosgene, dichloromethane, triethylamine, 0° C.;
1g: NaH or sodium acetate or triethylamine, dichloromethane or dry dimethylformamide, $R_2$—COCl or $R_2$—C(O)OC(O)$R_2$;
1h: Triethylamine, dichloromethane, $R_2$—$SO_2Cl$;
1i: Dry benzene or dichloromethane, triethylamine, potassium fluoride, $R_8$—NCO;
1j: Dichloromethane, triethylamine, $R_8$—NCS.

The compound of formula (A2) can be prepared by reacting nitromethane in presence of alkali metal hydroxide such as NaOH at 0° C. to room temperature; then pouring the product into conc. HCl at 0-10° C. and adding the compound of the formula (A1) in aqueous acid such as water-HCl mixture, and stirring at 0° C. to room temperature.

The compound of formula (A2) can be reacted with an acid anhydride such as acetic anhydride in presence of alkali metal salt such as potassium acetate or sodium acetate at 80-140° C. to obtain compound of formula (A3).

The compound of formula (A4) can be prepared by reacting compound of formula (A3) with a halogenating agent, for example with chlorinating agent such as $POCl_3$ at 80-140° C.

The compound of formula (A5) can be prepared by treating compound of formula (A4) with an amine of formula $R_1$—$NH_2$, in presence of acetic acid, wherein $R_1$ is as defined for formula (I) at 0-40° C.

An amine of formula (A6) can be prepared by reducing compound of formula (A5) in presence of a catalyst such as palladium on carbon or Raney Nickel with hydrogen in an appropriate solvent, such as ethanol, methanol, tetrahydrofuran or mixture thereof.

The tricyclic compound of formula (A7) can be prepared by treating compound of formula (A6) with trichloromethylchloroformate or triphosgene in presence of a base such as triethylamine or trimethylamine in an appropriate solvent such as dichloromethane or chloroform.

The tricyclic compound of formula (A7) can be treated with compound of formula $R_2COCl$ or $R_2$—C(O)OC(O)$R_2$ in an appropriate solvent, such as dimethylformamide, dichloromethane, tetrahydrofuran, dimethylsulfoxide, acetonitrile or mixture thereof, in presence of base such as sodium hydride, potassium hydride, sodium acetate, potassium acetate, triethylamine or mixture thereof to obtain compound of formula (A8).

The tricyclic compound of formula (A7) can be treated with compound of formula $R_2SO_2Cl$, in presence of a base such as triethylamine, sodium carbonate, potassium carbonate or mixture thereof to obtain compound of formula (A9) wherein $R_2$ is as defined for formula (I).

The tricyclic compound of formula (A7) can be treated with compound of formula $R_8N$=C=O, in a solvent such as dichloromethane, benzene, terahydrofuran or mixture thereof, in presence of a base such as potassium fluoride, sodium hydride, potassium hydride, lithium diisopropylamide or mixture thereof to obtain compound of formula (A10), wherein $R_8$ is as defined for formula (I).

The tricyclic compound of formula (A7) can be treated with compound of formula $R_8N$=C=S, in a solvent such as dichloromethane, dimethylformamide, tetrahydrofuran or mixture thereof to obtain compound of formula (A11), wherein $R_8$ is as defined for formula (I).

When the compounds of the present invention represented by the general formula (I) contain one or more basic groups, i.e. groups which can be protonated, they can form an addition salt with an inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

Thus, when the compounds of the present invention represented by the general formula (I) contain an acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, arginine, guanidine, diethanolamine, choline and tromethamine [tris(hydroxymethyl)aminomethane].

The pharmaceutically acceptable salts of the present invention can be synthesized from the subject compound, which contains a basic or an acidic moiety, by conventional chemical methods. Generally the salts are prepared by contacting the free base or acid with desired salt-forming inorganic or organic acid or base in a suitable solvent or dispersant or from another salt by cation or anion exchange. Suitable solvents are, for example, ethyl acetate, ether, alcohols, acetone, tetrahydrofuran (THF), dioxane or mixtures of these solvents.

The present invention furthermore includes all solvates of the compounds of the formula (I), for example hydrates, and the solvates formed with other solvents of crystallization, such as alcohols, ethers, ethyl acetate, dioxane, dimethylformamide (DMF), or a lower alkyl ketone, such as acetone, or mixtures thereof.

Methods of Treatment

The compounds of the present invention are PI3K and/or mTOR and/or TNFα and/or IL-6 inhibitors and find use in the treatment of benign or malignant tumors and/or inflammation.

Compounds of the present invention can be used to reduce, inhibit, or diminish the proliferation of tumor cells, and thereby assist in reducing the size of a tumor. Benign or malignant tumors that can be treated by compounds of formula (I) include, but are not limited to bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, acute lymphoblastic leukemia, acute myeloid leukemia, liver cancer, medulloblastoma, neuroblastoma, brain tumors, non-Hodgkin's lymphoma, mantle cell lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer and small-cell lung cancer. Compounds of the formula (I) are also of use in the treatment of inflammatory diseases, for example psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin.

Compounds of the present invention may also be used for the treatment of other diseases or conditions, such as psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma.

According to another aspect of the present invention, there is provided a method for the treatment of diseases mediated by PI3K or mTOR, comprising administering to a mammal in need thereof a therapeutically effective amount of a compound of formula I or a pharmaceutically acceptable salt or a pharmaceutically acceptable solvate thereof.

According to another aspect of the present invention, there is provided a method for the treatment of cancer, wherein the cancer is selected from the group comprising of bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, acute lymphoblastic leukemia, acute myeloid leukemia, liver cancer, medulloblastoma, neuroblastoma, brain tumors, non-Hodgkin's lymphoma, mantle cell lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer and small-cell lung cancer comprising administering to a mammal in need thereof a therapeutically effective amount of a compound of formula I or a pharmaceutically acceptable salt or a pharmaceutically acceptable solvate thereof.

According to another aspect of the present invention, there is provided a method for the treatment of cancer, including lung cancer, non-small-cell lung cancer, prostate cancer, ovarian cancer, colorectal cancer, pancreatic cancer, breast cancer and glioblastoma comprising administering to a mammal in need thereof a therapeutically effective amount of a compound of formula I or a pharmaceutically acceptable salt or a pharmaceutically acceptable solvate thereof.

According to further aspect of the present invention, there is provided a method for the treatment of diseases mediated by TNF-α or IL-6, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of TNF-α or IL-6 related disorder selected from the group comprising of psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of diseases mediated by TNF-α or IL-6 selected from the group comprising of rheumatoid arthritis, Crohn's disease, ulcerative colitis, septic shock, psoriasis and atherosclerosis, comprising administering to a mammal in need thereof a therapeutically effective amount of a compound of formula (I) or a pharmaceutically acceptable salt or a pharmaceutically acceptable solvate thereof.

According to another aspect of the present invention, there is provided the use of a compound of formula (I) in the treatment of diseases mediated by PI3K and/or mTOR.

According to another aspect of the present invention, there is provided the use of a compound of formula (I) in the treatment of cancers wherein the cancer is selected from the group comprising of bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, acute lymphoblastic leukemia, acute myeloid leukemia, liver cancer, medulloblastoma, neuroblastoma, brain tumors, non-Hodgkin's lymphoma, mantle cell lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer and small-cell lung cancer.

According to another aspect of the present invention, there is provided the use of a compound of formula (I) in the treatment of cancers such as lung cancer, non-small-cell lung cancer, prostate cancer, ovarian cancer, colorectal cancer, breast cancer, pancreatic cancer and glioblastoma.

According to another aspect of the present invention there is provided the use of compound of formula (I) in the treatment of diseases mediated by TNF-α and/or IL-6.

According to another aspect of the present invention there is provided the use of compound of formula (I) in the treatment of diseases selected from the group comprising of psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma.

According to another aspect of the present invention, there is provided the use of a compound of formula (I) in the treatment of inflammation such as rheumatoid arthritis, Crohn's disease, ulcerative colitis, septic shock syndrome, psoriasis and atherosclerosis.

According to another aspect of the present invention there are provided methods for manufacture of medicaments comprising compounds of formula (I), which are useful for the treatment of cancers such as breast cancer, leukemia, lung cancer, gastric cancer, prostate cancer, pancreatic cancer, glioblastoma, colon cancer, head and neck squamous cell carcinoma, multiple myeloma, cervical carcinoma and melanoma.

According to another aspect of the present invention there are provided methods for manufacture of medicaments comprising compounds of formula (I), which are useful for the treatment of inflammation, including diseases such as rheumatoid arthritis, Crohn's disease, ulcerative colitis, septic shock syndrome and atherosclerosis.

Pharmaceutical Compositions and Methods

According to another aspect of the present invention there is provided a pharmaceutical composition, comprising a therapeutically effective amount of a compound of formula (I) or a pharmaceutically acceptable salt or a pharmaceutically acceptable solvate thereof and a pharmaceutically acceptable excipient or carrier.

The pharmaceutical preparations according to the invention are prepared in a manner known per se and familiar to one skilled in the art. Pharmaceutically acceptable inert inorganic and/or organic carriers and/or additives can be used in addition to the compounds of formula (I), and/or their physiologically tolerable salts. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, for example, about 5 to 70%, or from about 5 to about 30% by weight of the compound of the formula (I) and/or its physiologically tolerable salt. The amount of the active ingredient of the formula (I) and/or its physiologically tolerable salt in the pharmaceutical preparations normally is from about 1 to 1000 mg.

The dose of the compounds of this invention, which is to be administered, can cover a wide range. The dose to be administered daily is to be selected to suit the desired effect. A suitable dosage is about 0.001 to 100 mg/kg/day of the compound of formula (I) and/or their physiologically tolerable salt, for example, about 0.01 to 50 mg/kg/day of a compound of formula (I) or a pharmaceutically acceptable salt of the compound. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic or resulting in unacceptable side effects to the patient.

The pharmaceuticals can be administered orally, for example in the form of pills, tablets, coated tablets, lozenges, capsules, dispersible powders or granules, suspensions, emulsions, syrups or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredient of the general formula (I) and/or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of the general formula (I) and/or their physiologically tolerable salts. Furthermore, in addition to at least one compound of the general formula (I) and/or its physiologically tolerable salt, the pharmaceutical preparations can also contain one or more other therapeutically or prophylactically active ingredients.

By "pharmaceutically acceptable" it is meant the carrier, diluent, excipients, and/or salt must be compatible with the other ingredients of the formulation, and not deleterious to the recipient thereof.

According to another aspect of the present invention there is provided a pharmaceutical composition, comprising a therapeutically effective amount of a compound of formula (I) or a pharmaceutically acceptable salt or a pharmaceutically acceptable solvate thereof and at least one further pharmaceutically active compound, together with a pharmaceutically acceptable excipient or carrier. Pharmaceutically active compound in combination with one or more compound of formula (I) for treatment of cancer can be selected from, but not limited to, one or more of the following groups: (i) Kinase inhibitors such as gefitinib, imatinib, erlotinib, lapatinib, bevacizumab, avastin, sorafenib, Bcr-Abl kinase inhibitors or LY-317615 (ii) Alkylating agent such as, mitomycin C, busulfan, oxaliplatin, cisplatin, procarbazine or dacarbazine (iii) Antimetabolites such as, methotrexate, mercaptopurine, thioguanine, fludarabine phosphate, fluorouracil, vinblastine, vincristine or paclitaxel (iii) Antibiotics such as, anthracyclines, dactinomycin or bleomycin (iv) Hormonal agents such as, tamoxifen, flutamide, GnRH (Gonadotropin-Releasing Hormone) agonists or aromatase inhibitors or (v) Cancer vaccines such as, avicine, oregovomab or theratope.

Pharmaceutically active compound in combination with one or more compound of formula (I) for treatment of inflammatory disorder can be selected from, but not limited to, one or more of the following groups:

It is understood that modifications that do not substantially affect the activity of the various embodiments of this invention are included within the invention disclosed herein. Accordingly, the following examples are intended to illustrate but not to limit the present invention.

Experimental

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Nomenclature of the compounds exemplified in the present invention was derived from Chemdraw Ultra version 9.0.1 CambridgeSoft Corporation, Cambridge.

Unless otherwise stated all temperatures are in degree Celsius. Also, in these examples and elsewhere, abbreviations have the following meanings:

| List of abbreviations | | | |
|---|---|---|---|
| mmol | Millimolar | DMF | Dimethyl formamide |
| mL | Milliliter | THF | Tetrahydrofuran |
| g | Gram | MeOH | Methanol |
| $H_2$ | Hydrogen | $POCl_3$ | Phosphorus oxychloride |
| $CO_2$ | Carbon dioxide | $MgCl_2$ | Magnesium chloride |
| NaOH | Sodium hydroxide | DMSO | Dimethyl sulfoxide |
| $NaHCO_3$ | Sodium bicarbonate | Pet ether | Petroleum ether |
| $Na_2CO_3$ | Sodium carbonate | RT | Room Temperature (20-30° C.) |
| HCl | Hydrochloric acid | psi | pound per square inch |
| $H_2SO_4$ | Sulphuric acid | PBS | Phosphate buffer saline |
| $Na_2SO_4$ | Sodium sulphate | FCS | Fetal calf serum |
| DCM/$CH_2Cl_2$ | Dichloromethane | FBS | Fetal bovine serum |
| RPMI | Roswell Park Memorial Institute | ATP | Adenosine triphosphate |
| HRP | Horse Radish Peroxidase | ELISA | Enzyme Linked ImmunoSorbent Assay |
| LPS | Lipopolysaccharide | rpm | revolutions per minute |
| DATP | 2'-deoxyadenosine 5'-triphosphate | TLC | Thin Layer Chromatography |
| MTS | (3-(4,5-Dimethylthiazol-2-yl)-5-(3-carboxymethoxyphenyl)-2-(4-sulfonyl)-2H-tetrazolium) | | |
| Hepes | N-2-Hydroxyethylpiperazine-N'-2-ethanesulfonic acid | | |
| Mpk | Milligrams per kilograms | | |

Intermediates

Preparation A: 6-Bromo-4-chloro-3-nitroquinoline

Step 1: 5-Bromo-2-(2-nitrovinylamino)benzoic acid

A suspension of 2-Amino-5-bromobenzoic acid (50 g, 231 mmol) in water-HCl (37%) (10:1) was stirred for 8 hours and was filtered (solution 1). Nitromethane (17 g, 278 mmol) was added over 10 minutes to a mixture of ice (70 g) and NaOH (31 g, 775 mmol) at 0° C. under stirring. After stirring for 1 hour at 0° C. and 1 hour at RT, this solution was added to a mixture of ice (56 g) and 84 mL of HCl (37%) at 0° C. (solution 2). Solution 1 and 2 were combined and the reaction mixture was stirred for 18 hours at RT. The yellow precipitate was filtered, washed with water and dried at 40° C. to obtain the title compound. The crude product was used directly for the next step.

Yield: 25 g (38%).

Step 2: 6-Bromo-3-nitroquinolin-4-ol

5-Bromo-2-(2-nitrovinylamino)benzoic acid (Compound of step 1, 25 g, 87 mmol) and potassium acetate (10.5 g, 104 mmol) in acetic anhydride (112 mL, 1185 mmol) were stirred for 3 hours at 120° C. The precipitate was filtered, and washed with acetic acid till the filtrate was colorless. It was further washed with water and dried to obtain the title compound. Yield: 15 g (64%); $^1$H NMR (CDCl$_3$, 500 MHz): δ 9.275 (s, 1H), 8.611-8.615 (d, 1H, J=2 Hz), 8.100-8.118 (d, 1H, J=9 Hz), 8.026-8.048 (dd, 1H, J=8.5 Hz, 2 Hz).

Step 3: 6-Bromo-4-chloro-3-nitroquinoline

6-Bromo-3-nitroquinolin-4-ol (Compound of step 2, 20 g, 74.3 mmol) and $POCl_3$ (150 mL, 1613 mmol) were stirred for 45 minutes at 120° C. The mixture was cooled to RT and poured slowly into ice-water. The precipitate was filtered, washed with ice-cold water, and dissolved in $CH_2Cl_2$. The organic layer was washed with cold brine, and was dried over $Na_2SO_4$. The solvent was evaporated to dryness to obtain the title compound.

Yield: 8 g (38%); $^1H$ NMR ($CDCl_3$, 500 MHz): δ 9.275 (s, 1H), 8.611-8.615 (d, 1H, J=2 Hz), 8.100-8.118 (d, 1H, J=9 Hz), 8.026-8.048 (dd, 1H, J=8.5 Hz, 2 Hz).

Preparation B: 2-(4-Aminophenyl)-2-methylpropanenitrile

Step 1: 2-Methyl-2-(4-nitrophenyl)propanenitrile

4-Nitrophenyl acetonitrile (20 g, 123.45 mmol), tetrabutylammonium bromide (2.15 g, 6.6 mmol) and methyl iodide (58 g, 475.41 mmol) in $CH_2Cl_2$ (150 mL) were added to NaOH (13.5 g, 337.5 mmol) in water (130 mL). The reaction mixture was stirred for 20 hours at RT. The organic layer was separated, was dried over $Na_2SO_4$, and was evaporated to dryness. The residue was dissolved in diethylether, was filtered over celite and solvent was evaporated to obtain the title compound. Yield: 18 g (76%); $^1H$ NMR ($CDCl_3$, 300 MHz): δ 8.220-8.250 (d, 2H, J=9 Hz), 7.627-7.657 (d, 2H, J=9 Hz), 1.750 (s, 6H).

Step 2: 2-(4-Aminophenyl)-2-methylpropanenitrile

2-Methyl-2-(4-nitrophenyl)propanenitrile (Compound of step 1, 16 g, 84.1 mmol) and Raney-Ni (4.16 g) were shaken in THF-MeOH [(1:1), 160 mL] under 40 psi of hydrogen for 10 hours at RT. After completion of reaction, the catalyst was filtered-off and the solvent was evaporated to dryness. The crude product was purified by column chromatography (silica gel, ethyl acetate in hexane) to obtain the title compound as oil.

Yield: 10 g (74%); $^1H$ NMR (DMSO-$d_6$, 300 MHz): δ 7.091-7.119 (d, 2H, J=8.4 Hz), 6.533-6.561 (d, 2H, J=8.4 Hz), 5.135 (s, 2H), 1.568 (s, 6H); MS: m/z 161 ($M^+$).

Preparation C: 2-(4-(6-Bromo-3-nitroquinolin-4-ylamino)phenyl)-2-methylpropanenitrile 6-Bromo-4-chloro-3-nitroquinoline (Compound of Preparation A, 18 g, 62.6 mmol) and 2-(4-aminophenyl)-2-methylpropanenitrile (Compound of Preparation B, 11 g, 68.9 mmol) was dissolved in acetic acid (350 mL) and the mixture was stirred for 2 hours. Water was added and the yellow precipitate was filtered off. The precipitate was washed with water, saturated aqueous $NaHCO_3$ and water. The yellow solid was dried to obtain the title compound. Yield: 19 g (74%); $^1H$ NMR (DMSO-$d_6$, 300 MHz): δ 10.0 (s, 1H), 8.979 (s, 1H), 8.594 (s, 1H), 7.894-7.926 (d, 1H, J=9.6 Hz), 7.817-7.847 (d, 1H, J=9 Hz), 7.348-7.376 (d, 2H, J=8.4 Hz), 7.011-7.039 (d, 2H, J=8.4 Hz), 1.575 (s, 6H); MS: m/z 409 ($M^-$).

Preparation D: 2-(4-(3-Amino-6-bromoquinolin-4-ylamino)phenyl)-2-methylpropanenitrile 2-(4-(6-Bromo-3-nitroquinolin-4-ylamino)phenyl)-2-methylpropane nitrile (Compound of Preparation C, 16 g, 42 mmol) was hydrogenated using Raney-Ni (7 g), THF-MeOH [(1:1), 250 mL] under 25 psi of hydrogen for 1 hour at RT. After completion of the reaction, the catalyst was filtered-off and the filtrate was evaporated to dryness to obtain the title compound. Yield: 13 g (88%); $^1H$ NMR (DMSO-$d_6$, 300 MHz): δ 8.609 (s, 1H), 7.908 (s, 1H), 7.829-7.836 (d, 1H, J=2.1 Hz), 7.744-7.773 (d, 1H, J=8.7 Hz), 7.425-7.462 (dd, 1H, J=9 Hz, 2.1 Hz), 7.236-7.265 (d, 2H, J=8.7 Hz), 6.511-6.540 (d, 2H, J=8.7 Hz), 5.448 (s, 2H), 1.600 (s, 6H); MS: m/z 381 ($M^+$).

Preparation E: 4,6-Dichloro-3-nitroquinoline

Step 1: 5-Chloro-2-(2-nitrovinylamino)benzoic acid

A suspension of 2-amino-5-chlorobenzoic acid (50 g, 291.94 mmol) in $H_2O$—HCl (37%) (10:1) was stirred for 8 hours and filtered (Solution 1). Nitromethane (15.5 g, 350 mmol) was added over 10 minutes to an ice-bath cooled mixture of ice (70 g) and NaOH (35 g, 820 mmol). After stirring for 1 hour at 0° C. and 1 hour at RT, the solution was added at 0° C. to a mixture of ice (56 g) and HCl (37%) (Solution 2). Solution 1 and 2 were combined and the reaction mixture was stirred for 18 hours at RT. The yellow precipitate was filtered, washed with water and dried in vacuo at 40° C. to obtain the title compound. The crude product was used for next step.

Yield: 26 g (30%).

Step 2: 6-Chloro-3-nitroquinolin-4-ol

5-Chloro-2-(2-nitrovinylamino)benzoic acid (Compound of step 1, 24 g, 98.36 mmol) and potassium acetate (19.2 g, 196.72 mmol) in acetic anhydride (120 mL, 1200 mmol) were stirred for 3 hours at 120° C. The precipitate was filtered, washed with acetic acid and water and dried in vacuo to obtain the title compound. Yield: 15 g (64%); $^1H$ NMR (DMSO-$d_6$, 300 MHz): δ 13.142 (s, 1H), 9.32 (s, 1H), 8.159-8.166 (d, 1H, J=2.1 Hz), 7.822-7.859 (dd, 1H, J=8.7 Hz, 2.4 Hz), 7.734-7.763 (d, 1H, J=8.7 Hz); MS: m/z 225 ($M^+$).

Step 3: 4,6-Dichloro-3-nitroquinoline

6-Chloro-3-nitroquinolin-4-ol (Compound of step 2, 5 g, 22.42 mmol) in $POCl_3$ (150 mL, 493 mmol) was stirred for 45 min at 120° C. The mixture was cooled to RT and poured slowly into ice-water. The precipitate was filtered, washed with ice-cold water, and dissolved in $CH_2Cl_2$. The organic phase was washed with cold brine and dried over $Na_2SO_4$. The organic solvent was evaporated to dryness to obtain the title compound.

Yield: 4.8 g (88%).

Preparation F: 2-(4-(6-Chloro-3-nitroquinolin-4-ylamino)phenyl)-2-methylpropanenitrile A solution of 4,6-dichloro-3-nitroquinoline (Compound of Preparation E, 4.0 g, 16.46 mmol) and 2-(4-aminophenyl)-2-methylpropanenitrile (2.63 g, 16.46 mmol) in acetic acid (350 ml) was stirred for 2 hours. Water was added and the yellow precipitate was filtered off, washed with water and saturated aqueous $NaHCO_3$. The yellow solid was dried to obtain the title compound. Yield: 5 g (83%); $^1H$ NMR (DMSO-$d_6$, 300 MHz): δ 10.074 (s, 1H), 9.062 (s, 1H,), 8.552-8.558 (d, 1H, J=1.8 Hz), 7.995-8.025 (d, 1H, J=9 Hz), 7.875-7.912 (t, 1H), 7.437-7.466 (d, 2H, J=8.4 Hz), 7.100-7.128 (d, 2H, J=8.4 Hz), 1.664 (s, 6H).

Preparation G: 2-(4-(3-Amino-6-chloroquinolin-4-ylamino)phenyl)-2-methylpropanenitrile 2-(4-(6-Chloro-3-nitroquinolin-4-ylamino)phenyl)-2-methylpropanenitrile (Compound of Preparation F, 5 g, 13.6 mmol) and Raney-Ni (2 g) were shaken in 100 mL of THF-MeOH (1:1) under 25 psi of $H_2$ for 3 hours at RT. After completion of reaction, the catalyst was filtered-off and the filtrate was evaporated to dryness to obtain the title compound. Yield: 3.5 g (66%); $^1$H NMR (DMSO-$d_6$, 300 MHz): δ 8.599 (s, 1H), 7.892 (s, 1H), 7.816-7.846 (d, 1H, J=9 Hz), 7.655-7.663 (d, 1H, J=2.4), 7.312-7349 (dd, 1H, J=8.7 Hz, 2.4 Hz), 7.233-7.262 (d, 2H, J=8.7 Hz), 6.510-6.538 (d, 2H, J=8.4 Hz), 5.457 (s, 2H), 1.598 (s, 6H); MS: m/z 337 (M$^+$).

Preparation H: 4-Chloro-6-methyl-3-nitroquinoline

Step 1: 5-Methyl-2-(2-nitrovinylamino)benzoic acid

A suspension of 2-amino-5-methylbenzoic acid (5 g, 33.11 mmol) in $H_2O$—HCl (37%) (10:1) was stirred for 8 hours and filtered (Solution 1). Nitromethane (1.75 ml, 37.73 mmol) was added over 10 min to an ice-bath cooled mixture of ice (7 g) and NaOH (3.97 g, 99.9 mmol). After stirring for 1 hour at 0° C. and 1 hour at RT, the solution was added at 0° C. to ice (56 g) and HCl (37%, 84 mL) (Solution 2). Solution 1 and 2 were combined and the reaction mixture was stirred for 18 hours at RT. The yellow precipitate was filtered off, washed with water and dried in vacuum at 40° C. to obtain the title compound. The crude product was used for step 2. Yield: 3 g (41%); $^1$HNMR (DMSO-$d_6$, 300 MHz): δ 13.78 (bs, 1H), 12.944-12.989 (d, 1H, J=13.5 Hz), 7.973-8.040 (dd, 1H, J=13.4 Hz, 6.3 Hz), 7.819 (s, 1H), 7.623-7.652 (d, 1H, J=8.7 Hz), 7.460-7.548 (m, 1H), 6.700-6.721 (d, 1H, J=6.3 Hz), 2.402 (s, 3H); MS: m/z 223 (M$^{-1}$).

Step 2: 6-Methyl-3-nitroquinolin-4-ol

5-Methyl-2-(2-nitrovinylamino)benzoic acid (Compound of step 1, 1.5 g, 6.756 mmol) and potassium acetate (1.3 g, 13.51 mmol) were stirred in acetic anhydride (8 ml, 148 7 mmol) for 3 hours at 120° C. The precipitate was filtered and washed with acetic acid until the filtrate is colorless and then washed with water and dried in vacuo to obtain the title compound. Yield: 610 mg (64%); $^1$H NMR (DMSO-$d_6$, 300 MHz): δ 9.126 (s, 1H), 8.035 (s, 1H), 7.606 (s, 2H), 2.432 (s, 3H); MS: m/z 203 (M$^{-1}$).

Step 3: 4-Chloro-6-methyl-3-nitroquinoline

6-Methyl-3-nitroquinolin-4-ol (Compound of step 2, 610 mg) in $POCl_3$ (5 mL) was stirred for 45 min at 120° C. The mixture was cooled to RT and poured slowly into ice-water. The precipitate was filtered, washed with ice-cold water and dissolved in $CH_2Cl_2$. The organic phase was washed with cold brine, and the aqueous phase was discarded. After drying over $Na_2SO_4$, the organic solvent was evaporated to dryness to obtain the title compound. Yield: 600 mg (90%); $^1$HNMR (DMSO-$d_6$, 300 MHz: δ 9.299 (s, 1H), 8.192 (s, 1H,), 8.096-8.124 (d, 1H, J=8.4 Hz), 7.893-7.927 (dd, 1H, J=8.4 Hz, 1.8 Hz), 2.604 (s, 3H).

Preparation I: 2-Methyl-2-(4-(6-methyl-3-nitroquinolin-4-ylamino)phenyl)propanenitrile 4-Chloro-6-methyl-3-nitroquinoline (Compound of Preparation H, 660 mg, 2.97 mmol) and 2-(4-aminophenyl)-2-methylpropanenitrile (570 mg, 3.56 mmol) were dissolved in acetic acid (10 ml) and stirred for 2 hours. Water was added and the yellow precipitate was filtered off, washed with water, saturated aqueous $NaHCO_3$ and water. The yellow solid was dried to obtain the title compound. Yield: 600 mg (58%); $^1$H NMR (DMSO-$d_6$, 300 MHz): δ 9.952 (s, 1H,), 9.016 (s, 1H), 8.184 (s, 1H), 7.890-7.918 (d, 1H, J=8.4 Hz), 7.699-7.727 (d, 1H, J=8.4 Hz), 7.421-7.445 (d, 2H, J=7.2 Hz), 7.082-7.108 (d, 2H, J=7.8 Hz), 2.284 (s, 3H), 1.660 (s, 6H); MS: m/z 347 (M$^+$).

Preparation J: 2-(4-(3-Amino-6-methyl-quinolin-4-ylamino)phenyl)-2-methylpropanenitrile 2-(4-(6-Methyl-3-nitroquinolin-4-ylamino)phenyl)-2-methylpropanenitrile (Compound of Preparation 1,600 mg, 1.73 mmol) and 10% Pd—C (90 mg) were shaken in 15 mL of THF-MeOH (1:1) under 25 psi of hydrogen for 3 hours at RT. After completion of reaction, the catalyst was filtered-off and the filtrate was evaporated to dryness to obtain the title compound. Yield: 250 mg (46%); $^1$H NMR (DMSO-$d_6$, 300 MHz): δ 8.507 (s, 1H), 7.819 (s, 1H), 7.698-7.726 (d, 1H, J=8.4 Hz), 7.641 (s, 1H), 7.211-7.239 (d, 2H, J=8.4 Hz), 7.164-7.198 (dd, 1H, J=8.4 Hz, 1.5 Hz), 6.503-6.532 (d, 2H, J=8.7 Hz), 5.178 (s, 2H), 2.358 (s, 3 Hs), 1.593 (s, 6H); MS: m/z 317 (M$^+$).

Intermediate 1: 2-(4-(8-Bromo-2-oxo-2,3-dihydro-1H-imidazo[4,5-c]quinolin-1-yl)phenyl)-2-methylpropanenitrile A solution of 2-(4-(3-amino-6-bromoquinolin-4-ylamino)phenyl)-2-methylpropanenitrile (Compound of Preparation D, 5 g, 13.1 mmol) and triethylamine (1.59 g, 15.7 mmol) in $CH_2Cl_2$ (120 mL) was added over 40 minutes to a solution of triphosgene (4.3 g, 14.4 mmol) in $CH_2Cl_2$ (80 mL) at 0° C. using ice-bath. The reaction mixture was stirred for 20 minutes at this temperature then was quenched with saturated aqueous $NaHCO_3$, stirred for 5 minutes and extracted with $CH_2Cl_2$. The organic layer was dried over $Na_2SO_4$, filtered and solvent was evaporated to obtain the title compound. Yield: 3.2 g (60%); $^1$H NMR (DMSO-$d_6$, 300 MHz): δ 11.835 (s, 1H), 8.783 (s, 1H), 7.908-7.938 (d, 1H, J=9 Hz), 7.810-7.838 (d, 2H, J=8.4 Hz), 7.665-7.694 (d, 2H, J=8.7 Hz), 7.613-7.650 (dd, 1H, J=9 Hz, 1.8 Hz), 6.949-6.955 (d, 1H, J=1.8 Hz), 1.609 (s, 6H); MS: m/z 406 (M$^+$).

Intermediate 2: 2-(4-(8-Chloro-2-oxo-2,3-dihydro-1H-imidazo[4,5-c]quinolin-1-yl)phenyl)-2-methylpropanenitrile A solution of 2-(4-(3-amino-6-Chloroquinolin-4-ylamino) phenyl)-2-methylpropanenitrile (Compound of Preparation G, 3.3 g, 9.8214 mmol) and triethylamine (1.34 g, 12.74 mmol) in $CH_2Cl_2$ (120 mL) was added over 40 min to a solution of triphosgene (3.5 g, 11.7852 mmol) in 80 mL of $CH_2Cl_2$ at 0° C. with an ice-bath. The reaction mixture was stirred for 20 min at this temperature then quenched with saturated aqueous $NaHCO_3$, stirred for 5 min and extracted with $CH_2Cl_2$. The organic layer was dried over $Na_2SO_4$, filtered and evaporated in vacuo to obtain the title compound. Yield: 1.2 g (34%); $^1$H NMR (DMSO-$d_6$, 300 MHz): δ 12.190 (s, 1H), 8.921 (s, 1H), 8.069-8.100 (d, 1H, J=8.7 Hz), 7.807-7.835 (d, 2H, J=8.4 Hz), 7.641-7.694 (m, 3H), 6.808-6.815 (d, 1H, J=2.1 Hz), 1.766 (s, 6H); MS: m/z 363 (M$^+$).

Intermediate 3: 2-Methyl-2-(4-(8-methyl-2-oxo-2,3-dihydro-1H-imidazo[4,5-c]quinolin-1-yl)phenyl) propanenitrile A solution of 2-(4-(3-amino-6-methyl-quinolin-4-ylamino)phenyl)-2-methylpropanenitrile (Compound of Preparation J, 190 mg, 0.6025 mmol) and triethylamine (0.12 ml, 0.901 mmol) in $CH_2Cl_2$ (10 mL) was added over 40 min to a solution of triphosgene (195 mg, 0.6139 mmol) in 5 mL of $CH_2Cl_2$ at 0° C. The reaction mixture was stirred for 20 min at this temperature then was quenched with saturated aqueous $NaHCO_3$, stirred for 5 min and extracted with $CH_2Cl_2$. The organic layer was dried over $Na_2SO_4$, filtered and evaporated in vacuo to obtain the title compound as brown solid. Yield: 145 mg (70%); $^1H$ NMR (DMSO-$d_6$, 300 MHz): δ 11.641 (s, 1H), 8.678 (s, 1H), 7.864-7.892 (d, 1H, J=8.4 Hz), 7.782-7.810 (d, 2H, J=8.4 Hz), 7.629-7.657 (d, 2H, J=8.4 Hz), 7.342-7.371 (d, 1H, J=8.7 Hz), 6.625 (s, 1H), 2.147 (s, 3H), 1.801 (s, 6H); MS: m/z 343 ($M^+$).

EXAMPLES

Example 1

2-(4-(8-Bromo-2-oxo-3-(4-(trifluoromethoxy)phenylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 0.12 mmol) and triethylamine 24.2 mg (0.24 mmol) in DCM (6 ml) was added 4-(trifluoromethoxy)benzene-1-sulfonyl chloride (46.8 mg, 0.18 mmol) at 0° C. The reaction was stirred at RT for 3 hours. The reaction mixture was poured into cold water and organic layer was separated. The aqueous layer was extracted with DCM. The combined organic layer was washed with brine dried over sodium sulfate and evaporated to dryness. The crude product was purified by column chromatography (silica gel, 2% acetone in chloroform) to obtain the title compound.

Yield: 28 mg (18%); $^1H$ NMR (DMSO-$d_6$, 300 MHz): δ 9.43 (s, 1H), 8.342-8.372 (dd, 1H, J=7.2, 1.8 Hz), 7.993-8.023 (d, 1H, J=9 Hz), 7.820-7.849 (d, 2H, J=8.7 Hz), 7.756-7.793 (dd, 1H, J=9, 2.1 Hz), 7.66-7.73 (m, 4H), 7.275-7.302 (d, 1H, J=8.1 Hz), 6.75-6.76 (d, 1H, J=2.1 Hz), 1.77 (s, 6H); MS: m/z 631 ($M^+$).

Example 2

2-(8-Bromo-1-(4-(2-cyanopropan-2-yl)phenyl)-2-oxo-1H-imidazo[4,5-c]quinolin-3 (2H)-ylsulfonyl) benzonitrile To a solution of 2-(4-(8-bromo-2-oxo-2,3-dihydro-1H-imidazo[4,5-c]quinolin-1-yl)phenyl)-2-methylpropanenitrile (Intermediate 1, 0.12 mmol) and triethylamine (0.36 mmol) in DCM (6 ml) was added 2-cyanobenzene-1-sulfonyl chloride (0.18 mmol) at 0° C. The reaction was stirred at RT for 3 hours. The reaction mixture was poured into cold water and organic layer was separated. The aqueous layer was extracted with DCM. The combined organic layer was washed with brine dried over sodium sulfate and evaporated to dryness. The crude product was purified by column chromatography (silica gel, 2% acetone in chloroform) to obtain the title compound.

Yield: 25 mg (36%); $^1H$ NMR (CDCl$_3$, 300 MHz): δ 9.72 (s, 1H), 8.51-8.538 (d, 1H, J=8.7 Hz), 8.02-8.05 (d, 1H, J=9 Hz), 7.83-7.93 (m, 3H), 7.729-7.757 (d, 2H, J=8.4 Hz), 7.66-7.69 (dd, 1H, J=9, 1.8 Hz), 7.474-7.502 (d, 2H, J=8.4 Hz), 7.019-7.025 (d, 1H, J=1.8 Hz), 1.81 (s, 6H); MS: m/z 572 ($M^+$).

Example 3

2-(4-(8-Bromo-2-oxo-3-(m-tolylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg 0.12 mmol) and triethylamine (24.2 mg, 0.24 mmol) in dichloromethane (6 ml) was added 3-methylbenzene-1-sulfonyl chloride (36 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 22 mg (32%); $^1H$ NMR (DMSO $d_6$, 300 MHz): δ 9.44 (s, 1H), 8.01 (s, 2H), 7.98 (s, 1H), 7.813-7.841 (d, 2H, J=8.4 Hz), 7.70-7.77 (m, 3H), 7.56-7.66 (m, 2H), 6.76-6.766 (d, 1H, J=1.8 Hz), 2.405 (s, 3H), 1.776 (s, 6H); MS: m/z 561 ($M^+$).

Example 4

2-(4-(8-Bromo-3-(2-methyl-5-nitrophenylsulfonyl)-2-oxo-2,3-dihydro-1H-imidazo[4,5-c]quinolin-1-yl) phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 2-methyl-5-nitrobenzene-1-sulfonyl chloride (53 mg, 0.18 mmol) at 0° C. The reaction was stirred at RT for 3 hours. The reaction mixture was poured into cold water and organic layer was separated. The aqueous layer was extracted with dichloromethane. The combined organic layer was dried over sodium sulfate and crude product was purified by column chromatography (silica gel, 2% acetone in chloroform) to obtain the title compound.

Yield: 35 mg (47%); $^1H$ NMR (DMSO-$d_6$, 300 MHz): δ 9.39 (s, 1H), 8.83-8.844 (d, 1H, J=2.4 Hz), 8.488-8.524 (dd, 1H, J=8.4, 2.4 Hz), 7.98-8.009 (d, 1H, 9 Hz), 7.69-7.82 (m, 6H), 6.779-6.785 (d, 1H, J=1.8 Hz), 2.67 (s, 3H), 1.73 (s, 6H); MS: m/z 606 (M+1).

Example 5

2-(4-(8-Bromo-3-(3-fluoro-4-methylphenylsulfonyl)-2-oxo-2,3-dihydro-1H-imidazo[4,5-c]quinolin-1-yl) phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 3-fluoro-4-methylbenzene-1-sulfonyl chloride (37.5 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 36 mg (50%); $^1$H NMR (DMSO-d$_6$, 300 MHz): δ 9.4 (s, 1H), 7.92-7.98 (m, 3H), 7.784-7.7.812 (d, 2H, J=8.4 Hz), 7.67-7.74 (m, 3H), 7.59-7.64 (m, 1H), 6.72-6.726 (d, 1H, J=1.8 Hz), 2.17 (s, 3H), 1.74 (s, 6H); MS: m/z 579 (M$^+$).

Example 6

2-(4-(8-Bromo-3-(3,5-dimethylphenylsulfonyl)-2-oxo-2,3-dihydro-1H-imidazo[4,5-c]quinolin-1-yl) phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg (0.36 mmol) in dichloromethane (6 ml) was added 3,5-dimethylbenzene-1-sulfonyl chloride (0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 25 mg (33.33%); $^1$H NMR (CDCl$_3$, 300 MHz): δ 9.58 (s, 1H), 7.957-7.987 (d, 1H, J=9 Hz), 7.79 (s, 2H), 7.699-7.727 (d, 2H, J=8.4 Hz), 7.605-7.642 (dd, 1H, J=9 Hz, 2.1 Hz), 7.425-7.453 (d, 2H, J=8.4 Hz), 7.29 (s, 1H), 6.96 (d, 1H, J=1.8 Hz), 2.36 (s, 6H), 1.79 (s, 6H); MS: m/z 575 (M$^+$).

Example 7

2-(4-(8-Bromo-2-oxo-3-(phenylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added benzenesulfonyl chloride (31.8 mg, 0.18 mmol) at 0° C. The reaction was stirred at RT for 3 hours. The reaction mixture was poured into cold water and organic layer was separated. The aqueous layer was extracted with dichloromethane. The organic layer was dried on sodium sulfate and evaporated to dryness to obtain the title compound. Yield: 20 mg (29.7%); $^1$H NMR (CDCl$_3$, 300 MHz): δ 9.59 (s, 1H), 8.198-8.227 (d, 2H, J=8.7 Hz), 7.958-7.989 (d, 1H, J=8.7 Hz), 7.70-7.723 (d, 2H, J=6.9 Hz), 7.57-7.69 (m, 4H), 7.40-7.436 (d, 2H, J=8.7 Hz), 6.97-6.981 (d, 1H, J=2.1 Hz), 1.79 (s, 6H).

Example 8

2-(4-(8-Bromo-2-oxo-3-tosyl-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added 4-methylbenzene-1-sulfonyl chloride (35.02 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 17 mg (25.37%); $^1$H NMR (CDCl$_3$, 300 MHz): δ 9.59 (s, 1H), 8.085-8.113 (d, 2H, J=8.4 Hz), 7.97-8.001 (d, 1H, J=9 Hz), 7.707-7.735 (d, 2H, J=8.4 Hz), 7.621-7.659 (dd, 1H, J=9.3, 2.1 Hz), 7.422-7.450 (d, 2H, J=8.4 Hz), 7.351-7.378 (d, 2H, J=8.1 Hz), 6.989-6.996 (d, 1H, J=2.1 Hz), 2.43 (s, 3H), 1.81 (s, 6H); MS: ink 561 (M$^+$).

Example 9

2-(4-(8-Bromo-2-oxo-3-(thiophen-2-ylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added thiophene-2-sulfonyl chloride (32.88 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 14 mg (17.16%); $^1$H NMR (DMSO-d$_6$, 300 MHz): δ 9.37 (s, 1H), 8.229-8.246 (d, 1H, J=5.1 Hz), 8.160-8.172 (d, 1H, J=3.6 Hz), 7.982-8.012 (d, 1H, J=9 Hz), 7.822-7.850 (d, 2H, J=8.4 Hz), 7.779-7.785 (d, 1H, J=1.8 Hz), 7.720-7.748 (d, 2H, J=8.4 Hz), 7.31 (t, 1H, J=4.2 Hz), 6.763-6.770 (d, 1H, J=2.1 Hz), 1.78 (s, 6H).

Example 10

2-(4-(8-Bromo-3-(3-fluorophenylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added 3-fluoro benzenesulfonyl chloride (35 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine, dried over sodium sulfate and evaporated to dryness. The crude product was purified by column chromatography (silica gel, 2% acetone in chloroform) to obtain the title compound. Yield: 50 mg (44.99%); $^1$H NMR (CDCl$_3$, 300 MHz): δ 9.57 (s, 1H), 8.025-8.051 (d, 1H, J=7.8 Hz), 7.952-7.980 (d, 1H, J=8.4 Hz), 7.94 (m 1H,), 7.75 (d, 2H, J=9 Hz,), 7.63 7.674 (dd, 1H, J=9, 2.1 Hz), 7.56-7.61 (m, 1H), 7.438-7.466 (d, 2H, J=8.4 Hz), 7.38-7.42 (m, 1H), 6.99-6.996 (d, 1H, J=1.8 Hz), 1.80 (s, 6H); MS: m/z 565 (M$^+$).

Example 11

2-(4-(8-Bromo-2-oxo-3-(quinolin-8-ylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added quinoline-8-sulfonyl chloride (40.98 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 32 mg (36.26%); $^1$H NMR (DMSO-$d_6$, 300 MHz): δ 9.60 (s, 1H), 8.70-8.836 (dd, 1H, J=7.5, 1.2 Hz), 8.561-8.757 (m, 1H), 8.54 (s, 1H), 8.46-8.492 (dd, 1H, J=8.4, 1.2 Hz), 8.0.25-8.058 (d, 1H, J=9.3 Hz), 7.869-7.921 (t, 1H, J=7.8 Hz), 7.74-7.79 (m, 3H), 7.581-7.623 (m, 1H), 7.534-7.563 (d, 2H, J=8.7 Hz), 6.752-6.758 (d, 1H, J=1.8 Hz), 1.21 (s, 6H); MS: m/z 598 (M$^+$).

Example 12

2-(4-(3-(4-Acetylphenylsulfonyl)-8-bromo-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.36 mmol) in dichloromethane (6 ml) was added 4-acetylbenzene-1-sulfonyl chloride (35.35 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 12 mg (17%); $^1$H NMR (DMSO-$d_6$, 300 MHz): δ 9.44 (s, 1H), 8.316-8.344 (d, 2H, J=8.4 Hz), 8.18-8.208 (d, 2H, J=8.4 Hz), 7.985-8.015 (d, 1H, J=9 Hz), 7.810-7.838 (d, 2H, J=8.4 Hz), 7.751-7.782 (d, 1H, J=9.3), 7.695-7.722 (d, 2H, J=8.4 Hz), 6.74 (s, 1H), 2.63 (s, 3H), 1.77 (s, 6H); MS: m/z 589 (M$^+$).

Example 13

2-(4-(8-Bromo-2-oxo-3-(3-(trifluoromethyl)phenylsulfonyl)-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 3-trifluoromethylbenzene-1-sulfonyl chloride (44 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 45 mg (60%); $^1$H NMR (DMSO-$d_6$, 300 MHz): δ 9.466 (s, 1H), 8.523-8.550 (d, 1H, J=8.1 Hz), 8.475 (s, 1H), 8.241-8.268 (d, 1H, J=8.1 Hz), 7.971-8.020 (m, 2H), 7.668-7.989 (m, 5H), 6.749-6.756 (d, 1H, J=2.1 Hz), 1.773 (s, 6H); MS: m/z 615 (M$^+$), 617 (M+2).

Example 14

2-(4-(8-Bromo-3-(3-methoxyphenylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 3-methoxybenzene-1-sulfonyl chloride (37.08 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 30 mg (42%); $^1$H NMR (CDCl$_3$, 300 MHz): δ 9.566 (s, 1H), 7.951-7.981 (d, 1H, J=9 Hz), 7.757-7.784 (d, 1H, J=8.1 Hz), 7.636-7.729 (m, 3H), 7.606-7.643 (dd, 1H, J=9 Hz, 2.1 Hz), 7.419-7.479 (m, 3H,), 7.208-7.230 (m, 1H), 6.957-6.963 (d, 1H, 1.8 Hz), 3.833 (s, 3H), 1.795 (s, 6H); MS: m/z 546 [M$^+$-(OCH$_3$)].

Example 15

2-(4-(8-Bromo-3-(3-bromophenylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 3-bromobenzene-1-sulfonyl chloride (46 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 40 mg (52%); $^1$H NMR (DMSO-$d_6$, 300 MHz): δ 9.444 (s, 1H), 8.352 (s, 1H), 8.208-8.234 (d, 1H, J=7.8 Hz), 8.050-8.074 (d, 1H, J=7.2 Hz), 7.985-8.015 (d, 1H, J=9 Hz), 7.821-7.849 (d, 2H, J=8.4 Hz), 7.776-7.7.782 (d, 1H, 1.8 Hz), 7.643-7.714 (m, 3H), 6.753-6.759 (d, 1H, J=2.1 Hz), 1.777 (s, 6H); MS: m/z 625 (M$^+$).

Example 16

2-(4-(8-Bromo-3-(3,5-difluorophenylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.4 mg, 0.24 mmol) in dichloromethane (6 ml) was added 3,5-difluorobenzene-1-sulfonyl chloride (38.26 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 25 mg (35%); $^1$H NMR (CDCl$_3$, 300

MHz): δ 9.553 (s, 1H), 8.002-8.032 (d, 1H, J=9 Hz), 7.752-7.798 (m, 4H), 7.664-7.701 (dd, 1H, J=8.7, 2.1 Hz), 7.466-7.495 (d, 2H, J=8.7 Hz), 7.175 (m, 1H), 7.002-7.009 (d, 1H, J=2.1 Hz), 1.831 (s, 6H); MS: m/z 583 (M$^+$).

Example 17

2-(4-(8-Bromo-3-(2,4-difluorophenylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (49.75 mg, 0.49 mmol) in dichloromethane (6 ml) was added 2,4-difluorobenzene-1-sulfonyl chloride (52 mg, 0.25 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 30 mg (42%); $^1$H NMR (DMSO-d$_6$, 300 MHz): δ9.31(s, 1H), 8.21-8.24(m, 1H), 7.968-7.998 (d, 1H, J=9.0 Hz.), 7.63-7.81 (m, 6H), 7.374-7.440 (m, 1H), 6.741-6.748 (d, 1H, J=2.1 Hz), 1.77(s, 6H); Mass m/z: 583 (M$^+$).

Example 18

2-(4-(8-Bromo-3-(methylsulfonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (24.85 mg, 0.25 mmol) in dichloromethane (6 ml) was added methylsulfonyl chloride (28.20 mg, 0.25 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 28 mg (47%); $^1$H NMR (DMSO-d$_6$, 300 MHz): δ 9.214 (s, 1H), 7.953-7.984 (d, 1H, J=9.3 Hz), 7.85-7.88 (d, 2H, J=8.4 Hz), 7.72-7.76 (m, 3H), 6.771-6.778 (d, 1H, J=2.1 Hz), 3.3727 (s, 3H), 1.774 (s, 6H); MS: m/z 485 (M$^+$).

Example 19

2-(4-(8-Chloro-2-oxo-3-(m-tolylsulfonyl)-2,3-dihydro-1H-imidazo[4,5-c]quinolin-1-yl)phenyl)-2-methylpropanenitrile To a solution of 2-(4-(8-chloro-2-oxo-2,3-dihydro-1H-imidazo[4,5-c]quinolin-1-yl)phenyl)-2-methylpropanenitrile (Intermediate 2, 50 mg, 0.14 mmol) and triethylamine (28 mg, 0.28 mmol) in dichloromethane (6 ml) was added 3-methylbenzene-1-sulfonyl chloride (40 mg, 0.21 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 29 mg (40%); $^1$H NMR (CDCl$_3$, 300 MHz): δ 9.605 (s, 1H), 8.023-8.093 (m, 3H), 7.72-7.748 (dd, 2H, J=6.6 Hz, 1.8 Hz), 7.44-7.551 (m, 5H), 6.855-6.862 (d, 1H, J=2.1 Hz), 2.44 (s, 3H), 1.82 (s, 6H); MS: m/z 517 (M$^+$).

Example 20

2-(8-Chloro-1-(4-(2-cyanopropan-2-yl)phenyl)-2-oxo-1H-imidazo[4,5-c]quinolin-3(2H)-ylsulfonyl)benzonitrile To a solution of 2-(4-(8-chloro-2-oxo-2,3-dihydro-1H-imidazo[4,5-c]quinolin-1-yl)phenyl)-2-methylpropanenitrile (Intermediate 2, 50 mg, 0.14 mmol) and triethylamine (28 mg, 0.28 mmol) in dichloromethane (6 ml) was added 2-cyanobenzene-1-sulfonyl chloride (42 mg, 0.21 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 24 mg (33%); $^1$H NMR (CDCl$_3$, 300 MHz): δ 9.698 (s, 1H), 8.496-8.525 (d, 1H, 8.7 Hz), 8.093-8.123 (d, 1H, J=9 Hz), 7.823-7.920 (m, 3H), 7.71-7.739(d, 2H, J=8.7 Hz), 7.525-7.563 (dd, 1H, J=9.3, 2.1 Hz), 7.46-7.488(d, 2H, J=8.4 Hz), 6.863-6.870 (d, 1H, 2.1 Hz), 1.798 (s, 6H); MS: m/z 528 (M$^+$).

Example 21

2-Methyl-2-(4-(8-methyl-2-oxo-3-(m-tolylsulfonyl)-2,3-dihydro-1H-imidazo[4,5-c]quinolin-1-yl)phenyl)propanenitrile To a solution of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and triethylamine (60 mg, 0.58 mmol) in dichloromethane (6 ml) was added m-methylbenzene-1-sulfonyl chloride (83.5 mg, 0.44 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 25 mg (17%); $^1$H NMR (CDCl$_3$, 300 MHz): δ 9.551 (s, 1H), 8.046-8.095 (d, 3H, J=8.4 Hz), 7.762-7.791 (d, 2H, J=8.7 Hz), 7.354-7.575 (m, 5H), 6.670 (s, 1H), 2.436 (s, 3H), 2.212 (s, 3H), 1.855 (s, 6H); MS: m/z 497 (M$^+$).

Example 22

2-(4-(3-(3-Fluorophenylsulfonyl)-8-methyl-2-oxo-2,3-dihydro-1H-imidazo[4,5-c]quinolin-1-yl)phenyl)-2-methylpropanenitrile To a solution of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and triethylamine (60 mg, 0.58 mmol) in dichloromethane (6 ml) was added 3-fluorobenzene-1-sulfonyl chloride (84 mg, 0.44 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness.

The crude product was purified by column chromatography (silica gel, 2% acetone in chloroform) to obtain the title compound. Yield: 20 mg (14%); $^1$H NMR (DMSO-$d_6$, 300 MHz): δ 9.341 (s, 1H), 8.039-8.059 (d, 2H, J=6 Hz), 7.939-7.967 (d, 1H, J=8.4 Hz), 7.683-7.811 (m, 6H), 7.469-7.499 (d, 1H, J=9 Hz), 6.433 (s, 1H), 2.112 (s, 3H), 1.780 (s, 6H); MS: m/z 501 (M$^+$).

Example 23

2-Methyl-2-(4-(8-methyl-3-(2-methyl-5-nitrophenyl-sulfonyl)-2-oxo-2,3-dihydro-1H-imidazo[4,5-c]quinolin-1-yl)phenyl)propanenitrile To a solution of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and triethylamine (60 mg, 0.58 mmol) in dichloromethane (6 ml) was added 2-methyl-5-nitrobenzene-1-sulfonyl chloride (103.35 mg, 0.44 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 20 mg (12%); $^1$H NMR (CDCl$_3$, 300 MHz): δ 9.560 (s, 1H), 9.155-9.163 (d, 1H, J=2.4 Hz), 8.384-8.420 (dd, 1H, J=8.4, 2.4 Hz), 8.050-8.079 (d, 1H, J=8.7 Hz), 7.696-7.724 (d, 2H, J=8.4 Hz), 7.538-7.564 (d, 1H, J=7.8 Hz), 7.458-7.486 (d, 3H, J=8.4 Hz), 6.708 (s, 1H), 2.760 (s, 3H), 2.236 (s, 3H), 1.742 (s, 6H); MS: m/z 542 (M$^+$).

Example 24

2-Methyl-2-(4-(8-methyl-2-oxo-3-(quinolin-8-ylsulfonyl)-2,3-dihydro-1H-imidazo[4,5-c]quinolin-1-yl)phenyl)propanenitrile To a solution of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and triethylamine (60 mg, 0.58 mmol) in dichloromethane (6 ml) was added quinoline-8-sulfonyl chloride (100 mg, 0.44 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 32 mg (20%); $^1$H NMR (DMSO-$d_6$, 300 MHz): δ 9.468 (s, 1H), 8.700-8.729 (d, 1H, J=8.7 Hz), 8.539-8.558 (m, 2H), 8.449-8.479 (d, 1H, J=9 Hz), 7.974-8.004 (d, 1H, J=9 Hz), 7.864-7.916 (t, 1H), 7.716-7.744 (d, 2H, J=8.4 Hz), 7.519-7.600 (q, 1H), 7.470-7.491 (m, 3H), 6.435 (s, 1H), 2.118 (s, 3H), 1.743 (s, 6H); MS: m/z 534 (M$^+$).

Example 25

2-(4-(3-(4-Acetylphenylsulfonyl)-8-methyl-2-oxo-2,3-dihydro-1H-imidazo[4,5-c]quinolin-1-yl)phenyl)-2-methylpropanenitrile To a solution of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and triethylamine (60 mg, 0.58 mmol) in dichloromethane (6 ml) was added 4-acetylbenzene-1-sulfonyl chloride (103.75 mg, 0.44 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 50 mg (33%); $^1$H NMR (DMSO-$d_6$, 300 MHz): δ 9.347 (s, 1H), 8.299-8.325 (d, 2H, J=7.8 Hz), 8.175-8.202 (d, 2H, J=8.1 Hz), 7.940-7.969 (d, 1H, J=8.7 Hz), 7.778-7.803 (d, 2H, J=7.5 Hz), 7.665-7.691 (d, 1H, J=7.8), 7.466-7.495 (d, 2H, J=8.7 Hz), 6.427 (s, 1H), 2.624 (s, 3H), 2.110 (s, 3H), 1.776 (s, 6H); MS: m/z 525 (M$^+$).

Example 26

2-(4-(8-Bromo-3-(morpholine-4-carbonyl)-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 100 mg, 0.25 mmol) in dry DMF (5 mL), sodium hydride (12 mg, 0.27 mmol) was added at 0° C. under nitrogen atmosphere. After 15 minutes morpholine-4-carbonyl chloride (56.1 mg, 0.37 mmol) was added, and the reaction mixture was heated at 60° C. for 48 hours. The reaction mixture was concentrated in vacuum. The crude product was purified by column chromatography (silica gel, 3% acetone in chloroform) to obtain the title compound. Yield: 15 mg (11.73%); $^1$H NMR (CDCl$_3$, 300 MHz): δ 9.09 (s, 1H), 7.973-8.004 (d, 1H, J=9.3 Hz), 7.772-7.8 (d, 2H, J=8.4 Hz), 7.621-7.658 (dd, 1H, J=9 Hz, 2.1 Hz), 7.517-7.545 (d, 2H, J=8.4 Hz,), 7.057-7.064 (d, 1H, J=2.1 Hz), 3.67 (t, 4H,), 3.26 (t, 4H), 1.84 (s, 6H); MS: m/z 520 (M$^+$).

Example 27

(E)-2-(4-(8-Bromo-3-but-2-enoyl-2-oxo-2,3-dihydro-1H-imidazo[4,5-c]quinolin-1-yl)phenyl)-2-methylpropanenitrile A mixture of 2-(4-(8-bromo-2-oxo-2,3-dihydro-1H-imidazo[4,5-c]quinolin-1-yl)phenyl)-2-methylpropanenitrile (Intermediate 1, 470 mg, 1.16 mmol) and sodium acetate (95 mg, 1.16 mmol) was heated at 110-120° C. in crotonic anhydride (2 ml) for four hours. Reaction mixture was cooled to RT. Water was added and extracted with Ethyl acetate. Ethyl acetate layer was washed with brine, dried over sodium sulfate and concentrated. The crude product was purified by column chromatography (silica gel, 2% acetone in chloroform) to obtain the title compound. Yield: 305 mg (55%); $^1$H NMR (CDCl$_3$, 300 MHz): δ 9.819 (s, 1H), 7.946-7.976 (d, 1H, J=9 Hz), 7.666-7.795 (d, 2H, J=8.7 Hz), 7.606-7.643 (dd, 1H, J=9 Hz, 2.1 Hz), 7.49-7.576 (m, 3H), 7.35-7.47 (m, 1H), 7.00-7.01 (d, 1H,J=1.8 Hz), 2.038 (d, 3H, J=6 Hz), 1.833 (s, 6H); MS: m/z 475 (M$^+$).

Example 28

2-(4-(8-Bromo-2-oxo-3-(2-propylpentanoyl)-2,3-dihydro-1H-imidazo[4,5-c]quinolin-1-yl)phenyl)-2-methylpropanenitrile A mixture of 2-(4-(8-Bromo-2-oxo-2,3-dihydro-1H-imidazo[4,5-c]quinolin-1-yl)phenyl)-2-methylpropanenitrile (Intermediate 1, 25 mg, 0.06 mmol) and sodium acetate (5 mg, 0.06 mmol) was heated at 110-120° C. in valproic anhydride (1 ml) for four hours. Reaction mixture was cooled to RT. Water was added and extracted with ethyl acetate. Ethyl acetate layer was washed with brine, dried over sodium sulfate and concentrated. The crude product was purified by column chromatography (silica gel, 2% acetone in chloroform) to obtain the title compound. Yield: 12 mg (38%); $^1$H NMR (CDCl$_3$, 300 MHz): δ 9.849 (s, 1H), 7.98-8.01 (d, 1H, J=9 Hz), 7.78-7.81 (d, 2H, J=8.7 Hz), 7.63-7.67 (dd, 1H, J=9, 2.1 Hz), 7.54-7.57 (d, 2H, J=8.1 Hz), 7.02-7.03 (d, 1H, J=1.8 Hz), 2.38 (m, 1H), 1.84 (s, 6H), 1.67 (m, 4H), 1.49 (m, 4H), 0.9 (m, 6H); MS: m/z 533 (M$^+$).

Example 29

(E)-2-(4-(8-Bromo-3-cinnamoyl-2-oxo-2,3-dihydro-1H-imidazo[4,5-c]quinolin-1-yl)phenyl)-2-methylpropanenitrile To a solution of 2-(4-(8-bromo-2-oxo-2,3-dihydro-1H-imidazo[4,5-c]quinolin-1-yl)phenyl)-2-methylpropanenitrile (Intermediate 1, 30 mg, 0.074 mmol) and triethylamine (70 mg, 0.69 mmol) in dichloromethane (6 ml) was added cinnamoyl chloride (18 mg, 148 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain title compound. $^1$H NMR (CDCl$_3$, 300 MHz): δ 9.921 (s, 1H), 8.204-8.257(d, 1H ,J=15.9 Hz), 8.071-8.123 (d, 1H,J=15.6 Hz), 7.983-8.013 (d, 1H J=9 Hz), 7.806-7.834 (d, 2H, J=8.4 Hz), 7.63-7.68 (m, 3H), 7.569-7.597 (d, 2H,J=8.4 Hz), 7.396-7.412 (m, 3H), 7.059-7.066 (d, 1H, J=2.1 Hz), 1.858 (s, 6H); MS: m/z 539 (M$^+$).

Example 30

2-(4-(3-Benzoyl-8-bromo-2-oxo-2,3-dihydro-1H-imidazo[4,5-c]quinolin-1-yl)phenyl)-2-methylpropanenitrile Sodium hydride (30 mg, 0.75 mmol) was added to dry DMF (5 ml) in a nitrogen atmosphere. The reaction flask was cooled in an ice-bath to 0° C., and 2-(4-(8-bromo-2-oxo-2,3-dihydro-1H-imidazo[4,5-c]quinolin-1-yl)phenyl)-2-methylpropanenitrile (Intermediate 1, 100 mg, 0.25 mmol) was added. After 15 minutes benzoyl chloride (42 mg, 0.29 mmol) was added, and the reaction mixture was heated at 50° C. for 24 hours. The reaction mixture was concentrated in vacuum. The crude product was purified by column chromatography (silica gel, 2% acetone in chloroform) to obtain the title compound. Yield: 13 mg (10%); $^1$H NMR (DMSO-d$_6$, 300 MHz): δ 9.410 (s, 1H), 7.998-8.028 (d, 1H, J=9 Hz), 7.939-7.963 (d, 2H, J=7.2 Hz), 7.848-7.876 (d, 2H, J=8.4 Hz), 7.764-7.792 (d, 3H, J=8.4 Hz), 7.644-7.669 (m, 1H), 7.48-7.56 (m, 2H), 6.865-6.872 (d, 1H, J=2.1 Hz), 1.78 (s, 6H); MS: m/z 511 (M+1).

Example 31

8-Bromo-1-(4-(2-cyanopropan-2-yl)phenyl)-N-(4-methoxyphenyl)-2-oxo-1H-imidazo[4,5-c]quinoline-3(2H)-carboxamide To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (18.18 mg, 0.18 mmol) in dichloromethane (6 ml) was added 1-isocyanato-4-methoxybenzene (26.82 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound Yield: 25 mg (22.82%); $^1$H NMR (DMSO-d$_6$, 300 MHz): δ 8.785 (s, 1H), 7.81-7.94 (m, 4H), 7.62-7.69 (m, 3H), 6.95 (s, 1H), 6.47-6.63 (m, 4H), 3.51 (s, 3H), 1.79 (s, 6H); MS: m/z 556 (M$^+$).

Example 32

N-benzyl-8-bromo-1-(4-(2-cyanopropan-2-yl)phenyl)-2-oxo-1H-imidazo[4,5-c]quinoline-3(2H)-carboxamide To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (18 mg, 0.18 mmol) in dichloromethane (6 ml) was added (isocyanatomethyl)benzene (24.57 mg, 0.18 mmol). The reaction mixture was stirred at RT for 2 hours. Then the reaction mixture was poured on to water. The organic layer was separated. The aqueous layer was extracted with dichloromethane. The combined organic layer was washed with brine, dried over sodium sulfate and evaporated to dryness. The crude product was purified by column chromatography (silica gel, 1% MeOH in chloroform) to obtain the title compound. Yield: 18 mg (20%); $^1$H NMR (CDCl$_3$, 300 MHz): δ 9.89 (s, 1H), 8.95 (t, 1H), 7.978-8.008 (d, 1H, J=9 Hz), 7.762-7.790 (d, 2H, J=8.4 Hz), 7.614-7.651 (dd, 1H, J=9, 1.8 Hz), 7.500-7.529 (d, 2H, J=8.7 Hz), 7.27-7.38 (m, 5H), 7.018-7.025 (d, 1H, J=2.1 Hz), 4.642-4.611 (d, 2H, J=5.7 Hz), 1.82 (s, 6H); MS: m/z 540 (M$^+$).

Example 33

8-Bromo-N-(2-bromophenyl)-1-(4-(2-cyanopropan-2-yl)phenyl)-2-oxo-1H-imidazo[4,5-c]quinoline-3(2H)-carboxamide To a suspension of 2-(4-(8-bromo-2-oxo-2,3-dihydro-1H-imidazo[4,5-c]quinolin-1-yl)phenyl)-2-methylpropanenitrile (Intermediate 1, 0.050 g, 0.12 mmol) and potassium fluoride (0.010 g, 0.18 mmol) in dry benzene (6 ml) was added 1-bromo-2-isocyanatobenzene (0.036 g, 0.12 mmol) at RT. The reaction was stirred at reflux temperature for 6 hours. The reaction mixture was cooled and poured into cold water, extracted with ethyl acetate (2×20 ml). Organic layer was washed with water dried over sodium sulfate and concentrated. The crude product was crystallized in ethyl acetate\pet ether to obtain the title compound. Yield: 0.017 g (22%); $^1$H NMR (DMSO-d$_6$, 300 MHz): δ 11.82 (s, 1H), 8.78 (s, 1H), 7.90 (d, 1H, J=9 Hz), 7.81 (d, 2H, J=8.1 Hz), 7.61-7.65 (m, 3H), 7.28 (d, 1H, J=8.1 Hz), 6.95-7.05 (m, 2H), 6.74 (d, 1H, 7.8 Hz), 6.41 (t, 1H, 7.2 Hz), 1.79 (s, 6H); MS: m/z 606 (M$^+$).

Example 34

8-bromo-N-(2-chloroethyl)-1-(4-(2-cyanopropan-2-yl)phenyl)-2-oxo-1H-imidazo[4,5-c]quinoline-3(2H)-carboxamide To a suspension of 2-(4-(8-bromo-2-oxo-2,3-dihydro-1H-imidazo[4,5-c]quinolin-1-yl)phenyl)-2-methylpropanenitrile (Intermediate 1, 0.040 g, 0.10 mmol) and potassium fluoride (0.010 g, 0.17 mmol) in dry benzene (6 ml) was added 1-chloroethyl isocyanate (0.015 g, 0.14 mmol) at RT. The reaction was stirred at reflux temperature for 6 hours. The reaction mixture was cooled and poured into cold water, extracted with ethyl acetate (2×20 ml). Organic layer was washed with water dried over sodium sulfate and concentrated. The crude product was triturated with diethylether to obtain the title compound. Yield: 0.030 g (60%); $^1$H NMR (DMSO-d$_6$, 300 MHz): δ 9.654 (s, 1H), 8.80-8.91 (t, 1H), 7.97-8.00 (d, 1H, J=9 Hz), 7.877-7.905 (d, 2H, J=8.4 Hz), 7.775-7.803 (d, 2H, J=8.4 Hz), 7.725-7.763 (dd, 1H, J=9, 2.1 Hz), 6.805-6.811 (d, 1H, J=1.8 Hz), 3.80-3.84 (q, 2H), 3.533-3.574 (t, 2H), 1.809 (s, 6H); MS: m/z 514 (M$^+$).

Example 35

N-allyl-8-bromo-1-(4-(2-cyanopropan-2-yl)phenyl)-2-oxo-1H-imidazo[4,5-c]quinoline-3(2H)-carboxamide To a suspension of 2-(4-(8-bromo-2-oxo-2,3-dihydro-1H-imidazo[4,5-c]quinolin-1-yl)phenyl)-2-methylpropanenitrile (Intermediate 1, 0.040 g, 0.10 mmol) and potassium fluoride (0.009 g, 0.147 mmol) in dry benzene (6 ml) was added allylisocyanate (0.010 g, 0.10 mmol) at RT. The reaction was stirred at reflux temperature for 6 hours. The reaction mixture was cooled and poured into cold water, extracted with ethyl acetate (2×20 ml). Organic layer was washed with water dried over sodium sulfate and concentrated. The crude product was triturated with ethyl acetate, filtered and filtrate was purified by column chromatography (silica gel, 2% acetone in chloroform) to obtain the title compound. Yield: 0.020 g (41%); $^1$H NMR (DMSO-d$_6$, 300 MHz): δ 9.653 (s, 1H), 8.723-8.761 (t, 1H), 7.971-8.001 (d, 1H, J=9 Hz), 7.874-7.903 (d, 2H, J=8.7 Hz), 7.769-7.798 (d, 2H, J=8.7 Hz), 7.723-7.761 (dd, 1H, J=9, 2.1 Hz), 6.808-6.814 (d, 1H, J=1.8 Hz), 5.904-5.996 (m, 1H), 5.234-5.296 (dd, 1H, J=17.1, 1.2 Hz), 5.134-5.173 (dd, 1H, J=10.5, 1.2 Hz), 4.010-4.045 (t, 2H), 1.806 (s, 6H); MS: m/z 492 (M$^+$).

Example 36

2-(4-(3-Acetyl-8-chloro-2-oxo-2,3-dihydro-1H-imidazo[4,5-c]quinolin-1-yl)phenyl)-2-methylpropanenitrile A mixture of 2-(4-(8-chloro-2-oxo-2,3-dihydro-1H-imidazo[4,5-c]quinolin-1-yl)phenyl)-2-methylpropanenitrile (Intermediate 2, 80 mg, 0.22 mmol) and sodium acetate (27.06 mg, 0.33 mmol) was heated at 50° C. in acetic anhydride (2 ml) for 3 hours. Reaction mixture was cooled to RT. Water was added and extracted with chloroform. Chloroform layer was washed with brine, dried over sodium sulfate and concentrated. The crude product was purified by column chromatography (silica gel, 2% acetone in chloroform) to obtain the title compound. Yield: 26 mg (29%); $^1$H NMR (CDCl$_3$, 300 MHz): δ 9.796 (s, 1H), 8.039-8.070 (d, 1H, J=9.3 Hz), 7.764-7.792 (d, 2H, J=8.4 Hz), 7.499-7.537 (m, 3H), 6.861-6.868 (d, 1H, J=2.1 Hz), 2.822 (s, 3H), 1.83 (s, 6H); MS: m/z 405 (M$^+$).

Example 37

2-(4-(3-Benzoyl-8-chloro-2-oxo-2,3-dihydro-1H-imidazo[4,5-c]quinolin-1-yl)phenyl)-2-methylpropanenitrile Sodium hydride (22 mg, 0.557 mmol) was added to dry DMF (5 mL) in a nitrogen atmosphere. The reaction flask was cooled in an ice-bath to 0° C., and 2-(4-(8-chloro-2-oxo-2,3-dihydro-1H-imidazo[4,5-c]quinolin-1-yl)phenyl)-2-methylpropanenitrile (Intermediate 2, 100 mg, 0.27 mmol) was added. After 15 minutes benzoyl bromide (61 mg, 0.33 mmol) was added, and the reaction mixture was heated at 50° C. for 24 hours. The reaction mixture was concentrated in vacuum. The crude product was purified by column chromatography (silica gel, 2.5% acetone in chloroform) to obtain the title compound. Yield: 30 mg (23%); $^1$H NMR (DMSO-d$_6$, 300 MHz): δ 9.372 (s, 1H), 8.048-8.078 (d, 1H, J=9 Hz), 7.905-7.929 (d, 2H, J=7.2 Hz), 7.810-7.839 (d, 2H, J=8.7 Hz), 7.730-7.759 (d, 2H, J=8.7 Hz), 7.611-7.666 (m, 2H), 7.449-7.523 (m, 2H), 6.698-6.705 (d, 1H, J=2.1 Hz), 1.752 (s, 6H); MS: m/z 467 (M$^+$).

Example 38

(E)-2-(4-(3-But-2-enoyl-8-chloro-2-oxo-2,3-dihydro-1H-imidazo[4,5-c]quinolin-1-yl)phenyl)-2-methylpropanenitrile A mixture of 2-(4-(8-chloro-2-oxo-2,3-dihydro-1H-imidazo[4,5-c]quinolin-1-yl)phenyl)-2-methylpropanenitrile (Intermediate 2, 179 mg, 0.50 mmol) and sodium acetate (40 mg, 0.50 mmol) was heated at 110-120° C. in crotonic anhydride (2 ml) for 4 hours. Reaction mixture was cooled to RT. Water was added and extracted with ethyl acetate. Ethyl acetate layer was washed with brine, dried over sodium sulfate and concentrated. The crude product was purified by column chromatography (silica gel, 2% acetone in chloroform) to obtain the title compound. Yield: 84 mg (39%); $^1$H NMR (CDCl$_3$, 300 MHz): δ 9.813 (s, 1H), 8.028-8.058 (d, 1H, J=9 Hz), 7.76-7.79 (dd, 2H, J=8.7, 1.8 Hz), 7.49-7.54 (m, 3H), 7.37-7.49 (m, 2H), 6.86-6.87 (d, 1H, J=2.1 Hz), 2.018-2.037 (d, 3H, J=6 Hz), 1.832 (s, 6H); MS: m/z 431(M$^+$).

Example 39

(E)-2-(4-(3-But-2-enoyl-8-methyl-2-oxo-2,3-dihydro-1H-imidazo[4,5-c]quinolin-1-yl)phenyl)-2-methylpropanenitrile In a mixture of 2-(4-(8-methyl-2-oxo-2,3-dihydro-1H-imidazo[4,5-c]quinolin-1-yl)phenyl)-2-methylpropanenitrile (Intermediate 3, 100 mg, 0.29 mmol) and sodium acetate (28.77 mg, 35.5 mmol), crotonic anhydride (1 ml) was added drop-wise at RT and the reaction mixture was heated at 110° C. for 3 hours. The reaction mixture was passed through a silica gel column in chloroform as eluent to obtain the title compound.

Yield: 30 mg (26%); $^1$H NMR (DMSO-d$_6$, 300 MHz): δ 9.564 (s, 1H), 7.912-7.940 (d, 1H, J=8.4 Hz), 7.837-7.862 (d, 2H, J=7.5 Hz), 7.724-7.749 (d, 2H, J=7.5), 7.485 (s, 1H), 7.442-7.449 (d, 1H, J=2.1 Hz), 7.285-7.332 (m, 1H), 6.474 (s, 1H), 2.13 (s, 3H), 1.990-2.009 (d, 3H, J=5.7 Hz), 1.811 (s, 6H); MS: m/z 411 (M+1).

Example 40

8-Bromo-N-(2-chloroethyl)-1-(4-(2-cyanopropan-2-yl)phenyl)-2-oxo-1H-imidazo[4,5-c]quinoline-3(2H)-carbothioamide To a solution of 2-(4-(8-bromo-2-oxo-2,3-dihydro-1H-imidazo[4,5-c]quinolin-1-yl)phenyl)-2-methylpropanenitrile (Intermediate 1, 50 mg, 0.12 mmol) and triethylamine (18.18 mg, 0.18 mmol) in dichloromethane (6 ml) was added 1-chloro-2-isothiocyanatoethane (21.87 mg, 0.18 mmol) at 0° C. The reaction was stirred at RT for 3 hours. The reaction mixture was poured into cold water and organic layer was separated. The aqueous layer was extracted with dichloromethane. The combined organic layer was washed with brine dried over sodium sulfate and evaporated to dryness. The crude product was purified by column chromatography (silica gel, 2% acetone in chloroform) to obtain the title compound. Yield: 10 mg (15%); $^1$H NMR (CDCl$_3$, 300 MHz): δ 9.945 (s, 1H), 7.966-7.996 (d, 1H, J=9 Hz), 7.745-7.773 (d, 2H, J=8.4 Hz), 7.615-7.645 (dd, 1H, J=9, 2.1 Hz), 7.516-7.544 (d, 2H, J=8.4 Hz), 7.082-7.089 (d, 1H, J=2.1 Hz), 4.289-4.344 (t, 2H), 3.411-3.467 (t, 2H), 1.82 (s, 6H); MS: m/z 491 (M−HCl).

Pharmacology

The efficacy of the present compounds can be determined by a number of pharmacological assays well known in the art, such as described below. The exemplified pharmacological assays, which follow herein, have been carried out with the compounds of the present invention.

Example 41

Protocol for PI3Kα assay

The assay was designed as in the reference, Cell, 2006, 125, 733-47 (Supplemental Data), the disclosure of which is incorporated by reference for the teaching of the assay.

The kinase reaction was carried out in a 25 µL volume in a 1.5 mL microcentrifuge tube. The reaction mixture consisted of kinase buffer (10 mM Hepes, pH 7.5, 50 mM MgCl$_2$), 20 ng PI3Kα kinase (Millipore, USA), 12.5 µg phosphatidylinositol (PI), 10 µM ATP and 1 µCi $^{32}$γ P dATP. Compounds of Example 1-40 were added at concentrations (stock solution was prepared in DMSO and subsequent dilutions were made in kinase buffer) as mentioned in the table. The reaction mixture was incubated at 30° C. for 20 minutes and was terminated by adding 1:1 mixture of MeOH and chloroform. The tube contents were mixed on a vortex mixer and centrifuged at 10000 rpm for 2 minutes. 10 µL of the organic (lower) phase was spotted on to a TLC plate (silica, mobile phase: n-propanol and 2 M glacial acetic acid in 65:35 ratio). The plates were dried and exposed to an X-ray film. The bands appearing as a result of $^{32}$γ P incorporation in PI were quantitated using the QuantityOne (BioRad, USA) densitometry program. PI-103 (Calbiochem, USA) was used as a standard.

Results: % inhibition of PI3Kα at 100 nM and 1000 nM is indicated in Table 1.

TABLE 1

| Example No. | % inhibition of PI3Kα | Example No. | % inhibition of PI3Kα |
|---|---|---|---|
| At 100 nM | | | |
| 2 | + | 3 | + |
| 6 | ++ | 7 | + |
| 8 | + | 13 | + |
| 17 | + | 18 | + |
| 20 | + | 30 | ++ |
| 32 | + | 33 | ++ |
| 36 | + | 37 | + |

TABLE 1-continued

| Example No. | % inhibition of PI3Kα | Example No. | % inhibition of PI3Kα |
|---|---|---|---|
| At 1000 nM | | | |
| 27 | + | 38 | + |

% Inhibition Ranges
+ 50% ≥ % Inhibition ≥ 10%
++ % Inhibition > 50%

Conclusion: Certain compounds of the present invention were found to inhibit PI3K expression.

Example 42

PI3K and mTOR Activity Assay

The assay was designed as in the reference, Biochemical Journal, 2000, 350, 717-722, the disclosure of which is incorporated by reference for the teaching of the assay.

Seed cells (Ovarian cell line A2780, ATCC) were plated in a 96 well microtitre plate at a density of 50,000 cells/cm$^2$ in appropriate complete cell culture medium. The cells were allowed to adhere for 18-24 hours. The cells were allowed to starve for 24 hours. The cells were pretreated (in triplicates) with the compounds of Example 1-40 (stock solution was prepared in DMSO and subsequent dilutions were made in kinase buffer) at a concentration of 10 µM for one hour. Then the cells were stimulated with 20% FCS for 30 minutes. A typical assay would consist of a set of unstimulated cells, a set of stimulated cells and a set of cells treated with compounds of Example 1-40 and a set of cells treated with the stimulator. The medium was discarded. The cells were fixed with 100 µL of 3.7% formaldehyde for 15 minutes. The formaldehyde was discarded by inverting the plate and tapping it on a thick tissue paper layer to remove traces. The cells were washed and permeabilized with 200 µL PBS+Triton-X 100 solution (hereafter referred to as PBS-Triton, containing 0.1% triton-X 100 in 1×PBS) three times, incubating the cells each time for 5 minutes. 100 µL blocking solution (10% FCS in PBS-Triton) was added and incubated for 1 hour at 25° C. The blocking solution was discarded and cells were incubated with the primary antibody in PBS-Triton at a dilution of 1:500 for 1 hour at RT (25° C.). [The primary antibody is Phospho-AKT (Ser 473); Cell Signaling; USA, Cat. No. 9271]. The primary antibody solution was discarded and the cells were washed 3 times with PBS-Triton solution and incubated with the HRP-conjugated secondary antibody in PBS-Triton at a dilution of 1:500 for 1 hour at RT (25° C.). The cells were washed 3 times with PBS-Triton followed by two washes with PBS (to remove traces of triton-X 100). The OPD (o-phenylene diamine dihydrochloride) substrate was prepared for detection of the signal by dissolving one tablet set (two tablets) of SigmaFast OPD (Sigma, USA, Cat No. P9187) in 20 mL distilled water. It should be kept protected from light. 100 µL OPD solutions was added to the wells and the plate was incubated in the dark for 3-5 minutes (depending upon the development of the color). The reaction was stopped by adding 50 µL 2 NH$_2$SO$_4$. The absorbance was measured at 490 nm. The values were expressed in the treated samples, in terms of percentage or fold decrease in AKT phosphorylation with respect to the induced sample. PI-103 (Calbiochem, USA) was used as a standard.

Results: % Inhibition of PI3 kinase activity at 10 µM is indicated in Table 2.

% Inhibition of mTOR at 10 µM is indicated in Table 3.

TABLE 2

| Example No. | % Inhibition of PI3K α (Cell-based) at 10 μM | Example No. | % Inhibition of PI3K α (Cell-based) at 10 μM |
|---|---|---|---|
| 2 | + | 3 | + |
| 6 | + | 17 | ++ |
| 27 | ++ | 30 | + |
| 38 | ++ | | |

TABLE 3

| Example No. | % Inhibition of mTOR (Cell-based) at 10 μM | Example No. | % Inhibition of mTOR (Cell-based) at 10 μM |
|---|---|---|---|
| 27 | ++ | 30 | + |
| 37 | + | 38 | ++ |

% Inhibition Ranges
+ 50% ≥ % Inhibition ≥ 10%
++ % Inhibition > 50%

Example 43

Cytotoxicity Assay

Propidium Iodide Assay

The assay was designed as in the reference, Anticancer Drugs, 2002, 13, 1-8, the disclosure of which is incorporated by reference for the teaching of the assay.

Cells from cell lines as mentioned in the table given below were seeded at a density of 3000 cells/well in a white opaque 96-well plate. Following incubation at 37° C./5% $CO_2$ for a period of 18-24 hours, the cells were treated with various concentrations (stock solution was prepared in DMSO and subsequent dilutions were made in media as per ATCC guidelines) of the compounds of Example 1-40 was for a period of 48 hours. At the end of treatment, the spent culture medium was discarded, the cells were washed with 1×PBS and 200 μl of 7 μg/ml propidium iodide was added to each well. The plates were frozen at −70° C. for at least 24 hours. For analysis, the plates were brought to RT, allowed to thaw and were read in PoleStar fluorimeter with the fluorescence setting. The percentage of viable cells in the non-treated set of wells was considered to be 100 and the percentage viability following treatment was calculated accordingly. $IC_{50}$ values were calculated from graphs plotted using these percentages. Table 4 depicts the $IC_{50}$ values of compounds of Example 1-40 in individual cell lines.

The abbreviations for the Cell Lines as used in Table 4 are:

| Type of Cancer | Abbreviation | Cell Line | Abbreviation |
|---|---|---|---|
| Lung | C1 | A549 | C1a |
| | | H460 | C1b |
| Prostate | C2 | PC3 | C2a |
| Ovarian | C3 | A2780 | C3a |
| | | OVCAR 3 | C3b |
| Colon | C4 | HCT116 | C4a |
| Pancreatic | C5 | PANC 1 | C5a |
| | | AsPC 1 | C5b |
| | | BxPC3 | C5c |
| Breast | C6 | MDA MB 231 | C6a |
| | | MDA MB 468 | C6b |
| | | MCF7 | C6c |
| | | BT 549 | C6d |
| | | T47D | C6e |
| Glioblastoma | C7 | U 373 | C7a |
| | | U 87 MG | C7b |

TABLE 4

| | | Example No. | | | | | | | | | |
|---|---|---|---|---|---|---|---|---|---|---|---|
| Cell Lines | | 1 | 2 | 3 | 4 | 5 | 6 | 9 | 10 | 11 | 12 |
| C1 | C1a | -- | -- | ++ | ++ | ++ | + | ++ | ++ | + | ++ |
| | C1b | ++ | +++ | +++ | ++ | ++ | + | -- | -- | -- | ++ |
| C2 | C2a | ++ | +++ | +++ | ++ | ++ | ++ | -- | -- | -- | + |
| C3 | C3a | +++ | +++ | +++ | -- | -- | -- | +++ | ++ | + | ++ |
| | C3b | ++ | ++ | ++ | + | + | + | -- | -- | -- | -- |
| C4 | C4a | -- | -- | ++ | + | + | + | + | ++ | + | + |
| C5 | C5a | -- | -- | ++ | -- | -- | -- | + | + | + | -- |
| | C5b | -- | -- | ++ | -- | -- | -- | -- | -- | -- | -- |
| | C5c | -- | -- | +++ | -- | -- | -- | -- | -- | -- | -- |
| C7 | C7a | + | + | + | + | + | + | -- | -- | -- | -- |
| | C7b | -- | -- | ++ | ++ | ++ | + | -- | -- | -- | -- |

| | | Example No. | | | | | | | | |
|---|---|---|---|---|---|---|---|---|---|---|
| Cell Lines | | 13 | 15 | 17 | 18 | 19 | 21 | 22 | 23 | 24 |
| C1 | C1a | + | + | ++ | ++ | +++ | + | + | + | -- |
| | C1b | + | -- | ++ | +++ | ++ | -- | -- | -- | + |
| C2 | C2a | + | -- | ++ | ++ | ++ | -- | -- | -- | + |
| C3 | C3a | -- | + | +++ | +++ | -- | -- | -- | -- | + |
| | C3b | + | -- | -- | -- | + | -- | -- | -- | -- |
| C4 | C4a | + | ++ | ++ | ++ | + | + | + | + | + |
| C5 | C5a | -- | + | -- | -- | -- | -- | -- | -- | -- |
| | C5b | -- | -- | ++ | ++ | -- | -- | -- | -- | -- |
| | C5c | -- | -- | ++ | ++ | + | -- | -- | -- | -- |
| C7 | C7a | + | -- | -- | -- | -- | -- | -- | -- | -- |
| | C7b | + | -- | -- | -- | -- | -- | -- | -- | -- |

| | | Example No. | | | | | | | | |
|---|---|---|---|---|---|---|---|---|---|---|
| Cell Lines | | 25 | 27 | 30 | 31 | 33 | 36 | 37 | 38 | 39 |
| C1 | C1a | + | +++ | ++ | ++ | ++ | ++ | ++ | +++ | + |
| | C1b | + | +++ | +++ | -- | ++ | +++ | ++ | +++ | -- |
| C2 | C2a | + | +++ | ++ | -- | + | + | ++ | +++ | -- |
| C3 | C3a | + | + | +++ | + | -- | -- | -- | + | -- |
| | C3b | -- | +++ | +++ | -- | + | + | ++ | +++ | -- |
| C4 | C4a | -- | ++ | +++ | + | + | + | + | + | + |
| C5 | C5a | -- | +++ | ++ | + | -- | -- | -- | +++ | -- |
| | C5b | -- | +++ | ++ | -- | -- | -- | -- | +++ | -- |
| | C5c | -- | -- | +++ | -- | -- | -- | -- | -- | -- |
| C6 | C6a | -- | +++ | -- | -- | -- | -- | -- | +++ | -- |
| | C6b | + | -- | -- | -- | -- | -- | -- | -- | -- |
| | C6c | -- | +++ | -- | -- | -- | -- | -- | +++ | -- |
| | C6d | + | +++ | -- | -- | -- | -- | -- | +++ | -- |
| | C6e | -- | +++ | -- | -- | -- | -- | -- | +++ | -- |
| C7 | C7a | -- | -- | +++ | -- | + | + | + | -- | -- |
| | C7b | -- | -- | -- | -- | + | + | + | -- | -- |

$IC_{50}$ Ranges in μM
+ $IC_{50}$ > 3
++ 3 ≥ $IC_{50}$ > 1
+++ 1 ≥ $IC_{50}$
-- Not Tested

Example 44

In vitro Screening to Identify Inhibitors of IL-6 and TNF-α

Human Monocyte Assay

The assay was designed as in the reference, Physiol. Res., 2003, 52, 593-598, the disclosure of which is incorporated by reference for the teaching of the assay.

Peripheral blood mononuclear cells (hPBMC) were harvested from human blood and suspended in RPMI 1640 culture medium containing 10% FCS, 100 U/mL penicillin and 100 mg/mL streptomycin (assay medium). Monocytes in the hPBMCs were counted using a Coulter Counter following which the cells were resuspended at $2 \times 10^5$ monocytes/mL. A cell suspension containing $2 \times 10^4$ monocytes was aliquoted per well of a 96-well plate. Subsequently, the hPBMCs were incubated for 4-5 hours at 37° C. under 5% $CO_2$ (During the incubation, the monocytes adhered to the bottom of 96-well plastic culture plate). Following the incubation, the non-adherent lymphocytes were washed with assay medium and the adherent monocytes re-fed with assay medium. After a 48-hour incubation period (37° C., 5% $CO_2$), monocytes were pretreated with various concentrations of compounds of Example 1-40 (prepared in DMSO) or vehicle (0.5% DMSO) for 30 minutes and stimulated with 1 µg/ml LPS (*Escherchia coli* 0111:B4, Sigma Chemical Co., St. Louis, Mo.). The incubation was continued for 5 hours at 37° C., 5% $CO_2$. Supernatants were harvested, assayed for IL-6 and TNF-α by ELISA as described by the manufacturer (BD Biosciences, USA). Dexamethasone (10 µM) was used as standard for this assay. The 50% inhibitory concentration ($IC_{50}$) values were calculated by a nonlinear regression method. In all experiments, a parallel plate was run to ascertain the toxicity of compounds of Example 1-40. The toxicity was determined using the MTS assay as described in Am. J. Physiol. Cell Physiol., 2003, 285, C813-C822. The results are indicated in table 4 and 5.

Results: Several compounds in this series show potent anti-inflammatory activity as evidenced by (i) robust inhibition of induced cytokine production and (ii) greater than 10 fold difference between $IC_{50}$ for toxicity and $IC_{50}$ for cytokine inhibition.

Biological results for IL-6 and TNFα inhibition are indicated in Table 5 and Table 6 respectively.

TABLE 5

| Example No. | IL-6 ($IC_{50}$) | Example No. | IL-6 ($IC_{50}$) |
|---|---|---|---|
| 1 | ++ | 2 | +++ |
| 3 | +++ | 4 | +++ |
| 6 | + | 9 | ++ |
| 10 | + | 11 | + |
| 12 | + | 14 | +++ |
| 15 | +++ | 17 | +++ |
| 18 | +++ | 21 | +++ |
| 22 | ++ | 25 | + |
| 27 | ++++ | 30 | ++++ |
| 32 | + | 33 | + |
| 37 | ++++ | 38 | ++++ |
| 39 | ++++ | | |

TABLE 6

| Example No. | TNFα ($IC_{50}$) | Example No. | TNFα ($IC_{50}$) |
|---|---|---|---|
| 2 | ++++ | 27 | ++++ |
| 30 | ++++ | 33 | ++++ |
| 37 | ++++ | 38 | ++++ |

$IC_{50}$ Ranges in µM
+ $IC_{50} > 30$
++ $30 \geq IC_{50} > 10$
+++ $10 \geq IC_{50} > 1$
++++ $IC_{50} \leq 1$ Conclusion: Certain compounds of the present invention were found to be TNF-α and IL-6 inhibitors.

Example 45

In vivo Studies

In-vivo efficacy of the compounds of the present invention was tested in colorectal cancer (cell line HCT116) tumor model Animals were housed and cared for in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of the Research Center of Piramal Life Sciences Limited, Mumbai, India.

Compound storage: All the compounds including standard were stored at 4-8° C. in an amber colored bottle. The compounds in solutions were also maintained at 4-8° C. in a refrigerator. Sample for animal injection was made fresh everyday.

Dose preparation: Required compound was weighed and mixed with 0.5% (w/v) carboxymethyl cellulose (CMC) and triturated with Tween-20 (secundum artum) with gradual addition of water to make up the final concentration.

Efficacy study in SCID mice: Severely Combined Immune-Deficient (SCID strain-CBySmn.CB17-Prkdc$^{scid}$/J, The Jackson Laboratory, Stock #001803) male mice weighing about 20 g of 6-9 weeks old were used in the study.

HCT116 cells were grown in McCoy's 5A medium containing 10% fetal calf serum in 5% $CO_2$ incubator at 37° C. Cells were pelleted by centrifugation at 1000-rpm for 10 minutes. Cells were resuspended in sterile 1×PBS to get a count of $25 \times 10^6$ cells per mL, 0.2 mL of this cell suspension (corresponding to $5 \times 10^6$ cells) was injected by subcutaneous (s.c.) route in SCID mice. Mice were observed every alternate day for palpable tumor mass. Once the tumor size reached a size of 5-7 mm in diameter, animals were randomized into respective treatment groups. Dose was administered every day for 14 days. Tumor size was recorded on every second day.

Tumor weight (mg) was estimated according to the formula for a prolate ellipsoid: {Length (mm)×[width (mm)$^2$]× 0.5}assuming specific gravity to be one and π to be three.

Tumor growth in compound treated animals was calculated as

T/C (Treated/Control)×100% and Growth inhibition Percent (GI %) was [100−T/C %].

Certain representative compounds within the scope of the present invention show moderate to significant in vivo anti-tumor activity in HCT116 xenograft model.

| Example | % growth inhibition on 14$^{th}$ day | No. of mice per group | Dose (Oral) |
|---|---|---|---|
| 27 | 36 | 7 | 50 mpk |
| 30 | 35 | 7 | 50 mpk |
| 38 | 17 | 7 | 50 mpk |

Conclusion:
All three compounds showed oral efficacy.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula (I),

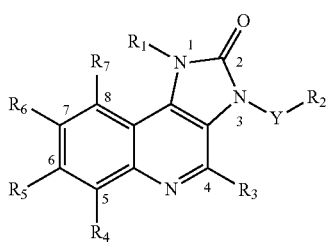

wherein
$R_1$ is phenyl substituted with —$C(CH_3)_2CN$;
$R_2$ is alkyl, alkenyl, aryl, heteroaryl, heterocyclyl, or —$NHR_8$;
$R_3$, $R_4$, $R_5$ and $R_7$ are hydrogen;
$R_6$ is hydrogen, alkyl, alkenyl, alkynyl, cycloalkyl, aralkyl, halogen, acyl, hydroxy, amino, cyano, nitro, thiol, —COOH, —$CONH_2$, —$OR_8$, —$NHR_8$, —$SR_8$ or —$B(OH)_2$;
$R_8$ at each occurrence is independently selected from alkyl, alkenyl, aralkyl or aryl; and
Y is —C(O), —C(S) or —$S(O)_2$;
wherein,
alkyl is unsubstituted or substituted with one or more of the same or different groups selected from halogen, nitro, cyano, amino, hydroxy, alkoxy, acyl, —$CONH_2$, or aryl;
alkenyl is unsubstituted or substituted with one or more of the same or different groups selected from alkyl, halogen, hydroxy, cyano, nitro, acyl, haloalkyl, alkoxy or aryl;
alkynyl is unsubstituted or substituted with one or more of the same or different groups selected from alkyl, halogen, hydroxy, cyano, nitro, acyl, haloalkyl, alkoxy or aryl;
cycloalkyl is unsubstituted or substituted with one or more of the same or different groups selected from halogen, nitro, cyano, amino, hydroxy, alkyl, alkoxy, haloalkyl, acyl, —$CONH_2$ or aryl;
aryl is unsubstituted or substituted with one or more of the same or different groups selected from cyano, nitro, halogen, alkyl, haloalkyl, hydroxy, alkoxy, haloalkoxy, acyl or aryl;
heteroaryl is unsubstituted or substituted with one or more of the same or different groups selected from cyano, nitro, alkyl, haloalkyl, alkoxy, hydroxy, halogen, amino, —$CONH_2$, carboxy, acyl or aryl;
heterocyclyl is unsubstituted or substituted with one or more of the same or different groups selected from cyano, nitro, halogen, alkyl, haloalkyl, hydroxy, alkoxy, amino, —$CONH_2$, carboxy, acyl or aryl; or
a stereoisomer, a tautomer, a pharmaceutically acceptable salt or a pharmaceutically acceptable solvate thereof.

2. A compound according to claim 1, wherein $R_6$ is halogen or alkyl; or a stereoisomer, a tautomer, a pharmaceutically acceptable salt or a pharmaceutically acceptable solvate thereof.

3. A compound according to claim 1, wherein Y is —$S(O)_2$; or a stereoisomer, a tautomer, a pharmaceutically acceptable salt or a pharmaceutically acceptable solvate thereof.

4. A compound according to claim 1, wherein Y is —C(O); or a stereoisomer, a tautomer, a pharmaceutically acceptable salt or a pharmaceutically acceptable solvate thereof.

5. A compound according to claim 1, wherein $R_2$ is —$NHR_8$, wherein $R_8$ is alkyl, alkenyl, aralkyl or aryl; a stereoisomer, a tautomer, a pharmaceutically acceptable salt or a pharmaceutically acceptable solvate thereof.

6. A compound according to claim 1 selected from:
2-(4-(8-bromo-2-oxo-3-(4-(trifluoromethoxy)phenylsulfonyl)-2,3-dihydro-1H-imidazo [4,5-c]quinolin-1-yl)phenyl)-2-methylpropanenitrile;
2-(8-bromo-1-(4-(2-cyanopropan-2-yl)phenyl)-2-oxo-1H-imidazo[4,5-c]quinolin-3(2H)-ylsulfonyl)benzonitrile;
2-(4-(8-bromo-2-oxo-3-(m-tolylsulfonyl)-2,3-dihydro-1H-imidazo[4,5-c]quinolin-1-yl) phenyl)-2-methylpropanenitrile;
2-(4-(8-bromo-3-(2-methyl-4-nitrophenylsulfonyl)-2-oxo-2,3-dihydro-1H-imidazo [4,5-c]quinolin-1-yl)phenyl)-2-methylpropanenitrile;
2-(4-(8-bromo-3-(3-fluoro-4-methylphenylsulfonyl)-2-oxo-2,3-dihydro-1H-imidazo[4,5-c]quinolin-1-yl)phenyl)-2-methylpropanenitrile;
2-(4-(8-bromo-3-(3,5-dimethylphenylsulfonyl)-2-oxo-2,3-dihydro-1H-imidazo[4,5-c]quinolin-1-yl)phenyl)-2-methylpropanenitrile;
2-(4-(8-bromo-2-oxo-3-(phenylsulfonyl)-2,3-dihydro-1H-imidazo[4,5-c]quinolin-1-yl) phenyl)-2-methylpropanenitrile;
2-(4-(8-bromo-2-oxo-3-tosyl-2,3-dihydro-1H-imidazo[4,5-c]quinolin-1-yl)phenyl)-2-methylpropanenitrile;
2-(4-(8-bromo-2-oxo-3-(thiophen-2-ylsulfonyl)-2,3-dihydro-1H-imidazo[4,5-c]quinolin-1-yl)phenyl)-2-methylpropanenitrile;
2-(4-(8-bromo-3-(3-fluorophenylsulfonyl)-2-oxo-2,3-dihydro-1H-imidazo[4,5-c]quinolin-1-yl)phenyl)-2-methylpropanenitrile;
2-(4-(8-bromo-2-oxo-3-(quinolin-8-ylsulfonyl)-2,3-dihydro-1H-imidazo[4,5-c]quinolin-1-yl)phenyl)-2-methylpropanenitrile;
2-(4-(3-(4-acetylphenylsulfonyl)-8-bromo-2-oxo-2,3-dihydro-1H-imidazo[4,5-c]quinolin-1-yl)phenyl)-2-methylpropanenitrile;
2-(4-(8-bromo-2-oxo-3-(3-(trifluoromethyl)phenylsulfonyl)-2,3-dihydro-1H-imidazo[4,5-c]quinolin-1-yl)phenyl)-2-methylpropanenitrile;
2-(4-(8-bromo-3-(3-methoxyphenylsulfonyl)-2-oxo-2,3-dihydro-1H-imidazo[4,5-c]quinolin-1-yl)phenyl)-2-methylpropanenitrile;
2-(4-(8-bromo-3-(3-bromophenylsulfonyl)-2-oxo-2,3-dihydro-1H-imidazo[4,5-c]quinolin-1-yl)phenyl)-2-methylpropanenitrile;
2-(4-(8-bromo-3-(3,5-difluorophenylsulfonyl)-2-oxo-2,3-dihydro-1H-imidazo[4,5-c]quinolin-1-yl)phenyl)-2-methylpropanenitrile;
2-(4-(8-bromo-3-(2,4-difluorophenylsulfonyl)-2-oxo-2,3-dihydro-1H-imidazo[4,5-c]quinolin-1-yl)phenyl)-2-methylpropanenitrile;

2-(4-(8-bromo-3-(methylsulfonyl)-2-oxo-2,3-dihydro-1H-imidazo[4,5-c]quinolin-1-yl) phenyl)-2-methylpropanenitrile;
2-(4-(8-chloro-2-oxo-3-(m-tolylsulfonyl)-2,3-dihydro-1H-imidazo[4,5-c]quinolin-1-yl) phenyl)-2-methylpropanenitrile;
2-(8-chloro-1-(4-(2-cyanopropan-2-yl)phenyl)-2-oxo-1H-imidazo[4,5-c]quinolin-3(2H)-ylsulfonyl)benzonitrile;
2-methyl-2-(4-(8-methyl-2-oxo-3-(m-tolylsulfonyl)-2,3-dihydro-1H-imidazo[4,5-c]quinolin-1-yl)phenyl)propanenitrile;
2-(4-(3-(3-fluorophenylsulfonyl)-8-methyl-2-oxo-2,3-dihydro-1H-imidazo[4,5-c]quinolin-1-yl)phenyl)-2-methylpropanenitrile;
2-methyl-2-(4-(8-methyl-3-(2-methyl-5-nitrophenylsulfonyl)-2-oxo-2,3-dihydro-1H-imidazo[4,5-c]quinolin-1-yl)phenyl)propanenitrile;
2-methyl-2-(4-(8-methyl-2-oxo-3-(quinolin-8-ylsulfonyl)-2,3-dihydro-1H-imidazo[4,5-c]quinolin-1-yl)phenyl)propanenitrile;
2-(4-(3-(4-acetylphenylsulfonyl)-8-methyl-2-oxo-2,3-dihydro-1H-imidazo[4,5-c]quinolin -1-yl)phenyl)-2-methylpropanenitrile;
2-(4-(8-bromo-3-(morpholine-4-carbonyl)-2-oxo-2,3-dihydro-1H-imidazo[4,5-c]quinolin-1-yl)phenyl)-2-methylpropanenitrile;
(E)-2-(4-(8-bromo-3-but-2-cnoyl)-2-oxo-2,3-dihydro-1H-imidazo[4,5-c]quinolin-1-yl) phenyl)-2-methylpropanenitrile;
2-(4-(8-bromo-2-oxo-3-(2-propylpentanoyl)-2,3-dihydro-1H-imidazo[4,5-c]quinolin-1-yl) phenyl)-2-methylpropanenitrile;
(E)-2-(4-(8-bromo-3-cinnamoyl-2-oxo-2,3-dihydro-1H-imidazo[4,5-c]quinolin-1-yl) phenyl)-2-methylpropanenitrile;
2-(4-(3-benzoyl-8-bromo-2-oxo-2,3-dihydro-1H-imidazo[4,5-c]quinolin-1-yl)phenyl)-2-methylpropanenitrile;
8-bromo-1-(4-(2-cyanopropan-2-yl)phenyl)-N-(4-methoxyphenyl)-2-oxo-1H-imidazo [4,5-c]quinoline-3(2H)-carboxamide;
N-benzyl-8-bromo-1-(4-(2-cyanopropan-2-yl)phenyl)-2-oxo-1H-imidazo[4,5-c]quinoline-3(2H)-carboxamide;
8-Bromo-N-(2-bromophenyl)-1-(4-(2-cyanopropan-2-yl) phenyl)-2-oxo-1H-imidazo[4,5-c]quinoline-3(2H)-carboxamide;
8-bromo-N-(2-chloroethyl)-1-(4-(2-cyanopropan-2-yl) phenyl)-2-oxo-1H-imidazo[4,5-c]quinoline-3(2H)-carboxamide;
N-allyl-8-bromo-1-(4-(2-cyanopropan-2-yl)phenyl)-2-oxo-1H-imidazo[4,5-c]quinoline-3(2H)-carboxamide;
2-(4-(3-acetyl-8-chloro-2-oxo-2,3-dihydro-1H-imidazo [4,5-c]quinolin-l-yl)phenyl)-2-methylpropanenitrile;
2-(4-(3-benzoyl-8-chloro-2-oxo-2,3-dihydro-1H-imidazo [4,5-c]quinolin-1-yl)phenyl)-2-methylpropanenitrile;
(E)-2-(4-(3-but-2-enoyl-8-chloro-2-oxo-2,3-dihydro-1H-imidazo[4,5-c]quinolin-1-yl) phenyl)-2-methylpropanenitrile;
(E)-2-(4-(3-but-2-enoyl-8-methyl-2-oxo-2,3-dihydro-1H-imidazo[4,5-c]quinolin- 1 -yl) phenyl)-2-methylpropanenitrile; and
8-bromo-N-(2-chloroethyl)-1-(4-(2-cyanopropan-2-yl) phenyl)-2-oxo-1H-imidazo[4,5-c]quinoline-3(2H)-carbothioamide; or
a stereoisomer, a tautomer, a pharmaceutically acceptable salt or a pharmaceutically acceptable solvate thereof.

7. A pharmaceutical composition, comprising a therapeutically effective amount of a compound of formula (I) according to claim 1 or a pharmaceutically acceptable salt or a pharmaceutically acceptable solvate thereof and a pharmaceutically acceptable excipient or carrier.

8. A method for the treatment of diseases mediated by PI3K or mTOR, wherein the disease is cancer and the cancer is selected from the group consisting of small-cell lung cancer, non-small-cell lung cancer, prostate cancer, ovarian cancer, colorectal cancer, pancreatic cancer, breast cancer and glioblastoma comprising administering to a mammal in need thereof, a therapeutically effective amount of a compound of formula (I) according to claim 1 or a pharmaceutically acceptable salt or a pharmaceutically acceptable solvate thereof.

9. A method for the treatment of disorders mediated by TNF-α or IL-6, wherein the TNF-α, mediated disorder or IL-6 related disorder is selected from the group consisting of rheumatoid arthritis, Crohn's disease, ulcerative colitis, septic shock, psoriasis and atherosclerosis comprising administering to a mammal in need thereof a therapeutically effective amount of a compound of formula (I) according to claim 1 or a pharmaceutically acceptable salt or a pharmaceutically acceptable solvate thereof.

10. A process for the preparation of a compound of formula (A 8)

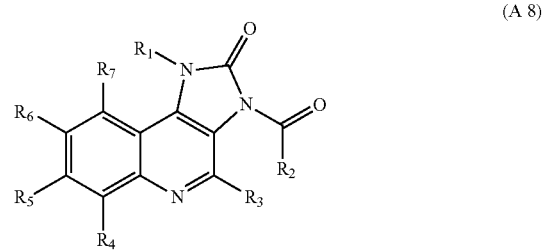

(A 8)

wherein, $R_2$ is alkyl, alkenyl, aryl, heterocyclyl or heteroaryl, $R_3$ is hydrogen, $R_1$, $R_4$, $R_5$, $R_6$, and $R_7$ are as defined for formula (I) according to claim 1, which comprises:
reacting a compound of formula (A7)

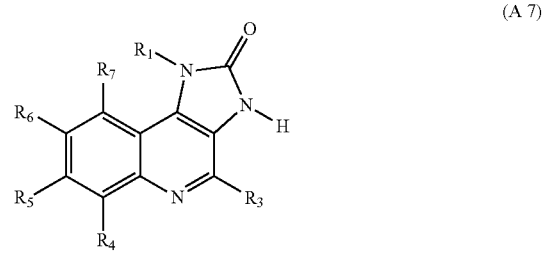

(A 7)

with a compound of formula $R_2COCl$, wherein $R_2$ is alkyl, alkenyl, aryl, heterocyclyl or heteroaryl, $R_3$ is hydrogen, $R_1$, $R_4$, $R_5$, $R_6$, and $R_7$ are as defined for formula (I) according to claim 1, in the presence of sodium hydride as the base and dimethylformamide (DMF) as the solvent to obtain the compound of formula (A8); and optionally converting the resulting compound into a pharmaceutically acceptable salt.

11. A process for the preparation of a compound of formula (A 9)

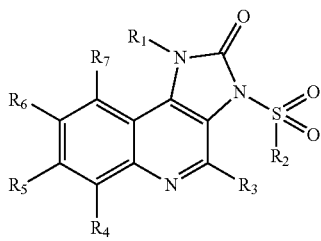

(A 9)

wherein, $R_3$ is hydrogen; $R_1$, $R_2$, $R_4$, $R_5$, $R_6$ and $R_7$ are as defined for formula (I), according to claim 1, which comprises:

reacting a compound of formula (A7)

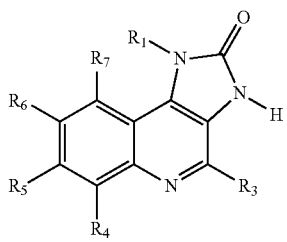

(A 7)

with a compound of formula $R_2SO_2Cl$, $R_3$ is hydrogen; $R_1$, $R_2$, $R_4$, $R_5$, $R_6$ and $R_7$ are as defined for formula (I), according to claim 1 in the presence of triethylamine as the base to obtain the compound of formula (A9); and optionally converting the resulting compound into a pharmaceutically acceptable salt.

12. A process for the preparation of a compound of formula (A 10)

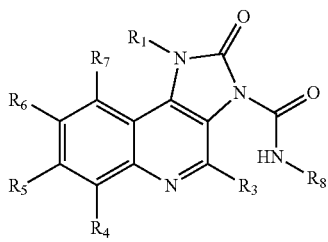

(A 10)

wherein, $R_3$ is hydrogen; $R_1$, $R_4$, $R_5$, $R_6$, $R_7$ and $R_8$ are as defined for formula (I), according to claim 1, which comprises:

reacting a compound of formula (A7)

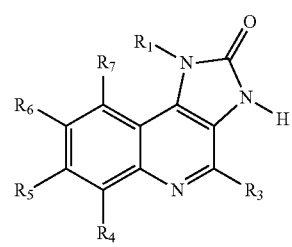

(A 7)

with a compound of formula $R_8N{=}C{=}O$, wherein $R_3$ is hydrogen; $R_1$, $R_4$, $R_5$, $R_6$, $R_7$ and $R_8$ are as defined for formula (I), according to claim 1 in the presence of benzene or dichloromethane (DCM) as a solvent to obtain the compound of formula (A 10); and optionally converting the resulting compound into a pharmaceutically acceptable salt.

13. A process for the preparation of a compound of formula (A 11)

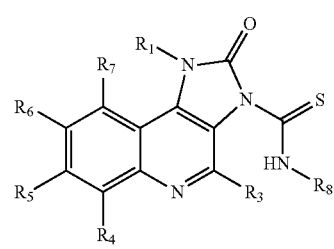

(A 11)

wherein, $R_3$ is hydrogen; $R_1$, $R_4$, $R_5$, $R_6$, $R_7$ and $R_8$ are as defined for formula (I), according to claim 1, which comprises:

reacting a compound of formula (A7)

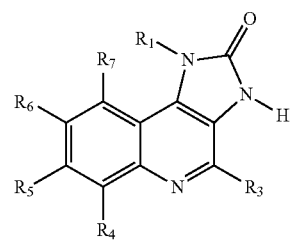

(A 7)

with a compound of formula $R_8N{=}C{=}S$, wherein $R_3$ is hydrogen; $R_1$, $R_4$, $R_5$, $R_6$, $R_7$ and $R_8$ are as defined for formula (I), according to claim 1 in the presence of dichloromethane (DCM) as a solvent to obtain the compound of formula (A 11); and optionally converting the resulting compound into a pharmaceutically acceptable salt.

* * * * *